US009632010B2

(12) United States Patent
Ding et al.

(10) Patent No.: US 9,632,010 B2
(45) Date of Patent: Apr. 25, 2017

(54) METHOD AND DEVICE FOR MONITORING THE MALFUNCTION OF APU TURBINE VANE FRACTURE AND ROTOR SHAFT JAM

(71) Applicant: AIR CHINA LIMITED, Beijing (CN)

(72) Inventors: Huifeng Ding, Beijing (CN); Zhuping Gu, Beijing (CN); Qihe Yue, Beijing (CN); Lei Chen, Beijing (CN); Jiaju Wu, Beijing (CN); Hailong Zhang, Beijing (CN); Fengliang Zheng, Beijing (CN); Lei Huang, Beijing (CN)

(73) Assignee: Air China Limited, Bejing (CN)

( * ) Notice: Subject to any disclaimer, the term of this patent is extended or adjusted under 35 U.S.C. 154(b) by 310 days.

(21) Appl. No.: 14/339,350

(22) Filed: Jul. 23, 2014

(65) Prior Publication Data
US 2015/0068293 A1    Mar. 12, 2015

(30) Foreign Application Priority Data
Jul. 24, 2013  (CN) .......................... 2013 1 0313840

(51) Int. Cl.
*G01M 15/14*    (2006.01)
*F01D 21/04*    (2006.01)
(Continued)

(52) U.S. Cl.
CPC .............. *G01M 15/14* (2013.01); *B64F 5/60* (2017.01); *F01D 21/04* (2013.01); *F02C 7/26* (2013.01);
(Continued)

(58) Field of Classification Search
CPC ....... G01M 15/14; B64F 5/0045; G01N 25/00
See application file for complete search history.

(56) References Cited

U.S. PATENT DOCUMENTS 6,122,575 A  *  9/2000  Schmidt .............. G06F 11/2252
                                          244/1 R
7,174,264 B2    2/2007  Yasukawa et al.
(Continued)

FOREIGN PATENT DOCUMENTS

CN    102320382 A    1/2012
CN    102343983 A    2/2012
(Continued)

OTHER PUBLICATIONS

European Search Report for Application No. 14178425.6 dated Dec. 18, 2014, 7 pages.
(Continued)

*Primary Examiner* — Freddie Kirkland, III
(74) *Attorney, Agent, or Firm* — Husch Blackwell LLP

(57) ABSTRACT

The present invention relates to a method and device for monitoring APU turbine vane fracture and rotor shaft jam. The method for monitoring APU turbine vane fracture and rotor shaft jam comprises: acquiring APU messages at multiple time points within a period; obtaining the operation parameters of the APU according to the APU messages, the operation parameters including at least the start time STA; calculating the average value AVG and the deviation index δ of the start time STA within the period; and determining the circumstance of the turbine vane fracture and rotation shaft jam of APU is in stable phase, decline phase or malfunction phase according to the deviation index δ.

20 Claims, 37 Drawing Sheets

(51) Int. Cl.
    *F02C 7/26*         (2006.01)
    *G05B 23/02*      (2006.01)
    *G01N 25/00*      (2006.01)
    *B64F 5/60*        (2017.01)

(52) U.S. Cl.
    CPC ......... *G01N 25/00* (2013.01); *G05B 23/0235* (2013.01); *F05D 2220/50* (2013.01); *F05D 2270/44* (2013.01)

(56) References Cited

U.S. PATENT DOCUMENTS

| | | | | |
|---|---|---|---|---|
| 7,369,932 B2* | 5/2008 | Kim | ............... | F01D 21/00 477/30 |
| 7,693,643 B2* | 4/2010 | Kim | ............... | F01D 21/14 60/778 |
| 8,061,650 B2* | 11/2011 | Nguyen | ............... | B64D 41/00 244/58 |
| 8,116,932 B2* | 2/2012 | Aldrich, III | ............... | F04B 17/05 417/24 |
| 8,471,702 B2* | 6/2013 | Babu | ............... | F02C 9/00 340/540 |
| 8,798,848 B2* | 8/2014 | Gu | ............... | G06F 17/00 701/29.4 |
| 2006/0195248 A1* | 8/2006 | Kim | ............... | F01D 21/14 701/100 |
| 2007/0260390 A1 | 11/2007 | Kim et al. | | |
| 2012/0161965 A1 | 6/2012 | Babu et al. | | |
| 2013/0179028 A1* | 7/2013 | Gu | ............... | G06F 17/00 701/29.4 |
| 2015/0013440 A1* | 1/2015 | Bianucci | ............... | G05B 23/0216 73/112.01 |

FOREIGN PATENT DOCUMENTS

| | | |
|---|---|---|
| CN | 102862685 A | 1/2013 |
| CN | 102866014 A | 1/2013 |
| CN | 102897327 A | 1/2013 |
| EP | 2544064 A2 | 1/2013 |

OTHER PUBLICATIONS

First office action for Chinese application No. 201310313840.9 dated Jul. 5, 2016, 8 pages.

\* cited by examiner

APU MES/IDLE REPORT <13>

| | A/C ID | DATE UTC | FROM | TO | FLT |
|---|---|---|---|---|---|
| | Plane No. | UTC Time | Flying | Ground | Fight No. |
| CC | BXXXX | yyyy-dd-mm xx:xx:xx | -- | -- | -- |
| | PH | CNT | CODE | BLEEDSTATUS | APU |
| | Segment | Count | Trigger Code | State of Bleed Air Valve | Bleed Air Valve of APU |
| C1 | 11 | 78401 | 4000 | 16 0000 1 00000 19 | 1 |
| | TAT | ALT | CAS | MN | GW | CG | DMU |
| | Total Temperature | Datum Mark | Calculation of airspeed | Mach Speed | Total Weight | Gravity Center | Version |
| CE | 23.3 | 150 | -- | -- | 65600 | 29.2 | 171CA2 |
| | ASN | AHRS | ACYC | PHAD | | | |
| | APU Serial Number | APU Hours | APU Cycle | APU Performance Adjustment | | | |
| E1 | 2056 | 18477 | 16894 | 4000 | | | |
| | ESN | ACW1 | ACW2 | NA | EGTA | IGV | |
| | Engine No. | Control Word 1 | Control Word 2 | Rotation Speed | Exhausted Gas Temperature | IGV Position | |
| N1 | 011909 | 00000 | 0A000 | 99.7 | 588 | -5 | |
| N2 | 011473 | 00000 | 0A000 | 99.8 | 580 | -5 | |
| N3 | 000000 | 00000 | 04000 | 99.6 | 388 | 82 | |
| | P2A | LCIT | WB | PT | LCDT | OTA | GLA |
| | Inlet Gas pressure | Inlet Temperature of Load Compressor | Bleed Air Flow | Bleed Air pressure | Outlet Temperature of Load Compressor | Lube Oil Temperature | APU Generator Load |
| S1 | .956 | 33 | .41 | 3.99 | XXXX | 110 | 33 |
| S2 | .952 | 32 | .41 | 3.99 | XXXX | 110 | 27 |
| S3 | .96 | 32 | 0 | 1.17 | XXXX | 107 | 0 |
| | STA | EGTP | NPA | OTA | ICIT | | |
| | PREVIOUS APU START (Parameters on start of APU) | | | | | | |
| | Start Time | EGT Peak Value | Rotation Speed at Peak Value of EGT | Lube Oil Temperature | Inlet Temperature of Load Compressor | | |
| V1 | 49 | 808 | 35 | 110 | 32 | | |

Figure 4

METHOD AND DEVICE FOR MONITORING THE MALFUNCTION OF APU TURBINE VANE FRACTURE AND ROTOR SHAFT JAM

TECHNICAL FIELD

The present invention relates to monitoring the malfunction of the aircraft component, in particular to method and device for monitoring the malfunction of turbine vane fracture and rotor shaft jam of aircraft auxiliary power unit.

BACKGROUND ART

Airborne Auxiliary Power Unit, abbreviated as APU, is a small turbine engine mounted on the tail of an aircraft. Its main function is to supply power and provide gas sources. Some APUs are capable of providing additive thrust to the aircraft. Specifically, before taking off from the ground, an aircraft may rely on a power and gas supply from the APU, rather than the ground power and gas source vehicles. While on the ground, the APU also supplies power and compressed air to ensure lighting and air-conditioning in the cabin and cockpit. During take-off of an aircraft, the APU can serve as a backup power source. After the aircraft is landed, lighting and air-conditioning of the aircraft are still maintained by power from the APU. The functions of APU influence the flight stability of the aircraft, which directly affects flight cost and quality of service of the aircraft.

The malfunction of APU turbine vane fracture and rotor shaft jam is a common malfunction of APU. When such malfunction occurs, the only solution is to replace the engine of APU, and therefore the maintenance cost is very expensive and usually twice with respect to the cost of normal repair. If the malfunction can be found in advance, the maintenance cost will be greatly reduced and the maintenance cycle will be shortened. The invention provides the monitoring method for the malfunction of turbine vane fracture and rotor shaft jam to meet the demands in the art.

SUMMARY

For the above technical problem existing in the prior art, there is provided, according to one aspect of the present invention, a method for monitoring the malfunction of turbine vane fracture and rotor shaft jam of aircraft auxiliary power unit, comprising: acquiring APU messages at multiple time points within a period; obtaining the operation parameters of the APU according to the APU messages, the operation parameters including at least the start time STA; calculating the average value AVG and the deviation index δ of the start time STA within the period; and determining the circumstance of the turbine vane fracture and rotation shaft jam of APU is in stable phase, decline phase or malfunction phase according to the deviation index δ.

According to the above method, wherein the step of determining the circumstances of APU turbine vane fracture and rotor shaft jam is in stable phase, decline phase or malfunction phase comprises: response to the deviation index δ is less than the threshold value of decline phase, determining the circumstances of APU turbine vane fracture and rotor shaft jam is in stable phase; response to the deviation index δ is greater than the threshold value of decline phase and less than the threshold value of malfunction, determining the circumstances of APU turbine vane fracture and rotor shaft jam is in decline phase; and response to the deviation index δ is greater than the threshold value of malfunction, determining the circumstances of APU turbine vane fracture and rotor shaft jam is in malfunction phase.

The method described above, further comprises: determining the deviation index δ when the circumstances of APU turbine vane fracture and rotor shaft jam is in stable phase; wherein the threshold value of decline is around 2 times than the deviation index, and the threshold value of malfunction is around 6 times than the stable deviation index.

The method described above, wherein, the decline phase further comprises serious decline phase, and the threshold value of serious decline phase is between the threshold values of decline and malfunction, response to the deviation index δ is greater than the threshold value of the serious decline and less than the threshold value of malfunction, determining the circumstances of APU turbine vane fracture and rotor shaft jam is in serious decline phase, the threshold value of the serious decline is around 4 times than the stable deviation index δ.

The method described above, wherein the time period of 2-3 points per day is about 5-10 days.

The method described above, wherein about 10-40 APU messages are obtained within the time period.

The method described above, further comprises: obtaining the start time STA on the next time point by updating the APU message at the next time point; response to STAnext is greater than AVG+nδ or less than AVG−nδ, determining whether the $STA_{next+1}$ obtained according to the further next message related to APU is greater than AVG+nδ or less than AVG−nδ; and response to the start time STA obtained according to the message related to APU is greater than AVG+nδ or less than AVG−nδ continuously and exceeding the predetermined number Z, issuing the warning.

The method described above, response to the start time STA obtained according to the message related to APU is between AVG+nδ or less than average value AVG−nδ, recalculating the average value AVG and deviation index δ of the start time STA.

The method described above, response to the start time STA obtained according to the message related to APU is greater than AVG+nδ or less than AVG−nδ continuously and exceeding the predetermined number Z, recalculating the average value AVG and deviation index δ of the start time STA.

The method described above, wherein the deviation index δ is standard deviation.

The method described above, wherein the value of n is 2 or 3.

The method described above, response to the start time STA obtained according to the message related to APU is greater than AVG+nδ or less than AVG−nδ continuously and exceeding the predetermined number Z, issuing the warning.

The method described above, wherein the value of Z is 3-5.

The method described above, further comprises: response to whether the highest exhaust gas temperature on start EGTP reaches the temperature at red line, issuing the warning of the malfunction of APU turbine vane fracture and rotor shaft jam.

The method described above, further comprises that: response to whether the Number of Proportion in APU NPA reaches or closes to the predetermined threshold value when EGT is at its peak on start, issuing the warning of the malfunction of APU turbine vane fracture and rotor shaft jam, wherein the predetermined threshold value is 35-40%.

The method described above, wherein response to the increase of the standard deviation of EGTP and NPA, issuing the warning of the malfunction of APU turbine vane fracture and rotor shaft jam.

The method described above, the method further comprises: response to that exhaust gas temperature EGT is close to the red line value or whether the angle of the inlet guide vane IGV appears an upward jump, issuing the warning of the malfunction of APU turbine vane fracture and rotor shaft jam.

The method described above, wherein the method further comprises: acquiring the history data of start time STA; and determining whether the start time STA exhibits gradual increase, gradual regular, and then discrete.

According to one aspect of the invention, a device for monitoring the circumstances of APU turbine vane fracture and rotor shaft jam is provided, which comprises: message acquiring unit, which acquires the APU messages within a time period; message analyzing unit, which analyses the required APU operation data, the operation data at least comprises start time STA; and malfunction monitoring unit, which determines the circumstances of APU turbine vane fracture and rotor shaft jam is in stable phase, decline phase or malfunction phase according to the APU operation data.

According to another aspect of the invention, a device for monitoring the circumstances of APU turbine vane fracture and rotor shaft jam is provided, which comprises: a processor; and a memory linked with the processor, which stores the computer-readable codes; the computer-readable codes run in the processor to execute the following steps: acquiring the APU messages at multiple time points within a time period; obtaining the operation parameters of the APU according to the APU message, the operation parameters at least comprises start time STA; calculating the average value AVG and deviation index δ of the start time STA within the time period; and determining that the circumstances of APU turbine vane fracture and rotor shaft jam is in stable phase, decline phase, serious decline phase or malfunction phase according to the deviation index δ.

DESCRIPTION OF DRAWINGS

Hereinafter, preferred embodiments of the present invention will be further described with reference to the accompany drawings, wherein:

FIG. 4 is drawing illustrating an example of the A13 message of Airbus;

MODE OF INVENTION

Figure 1:
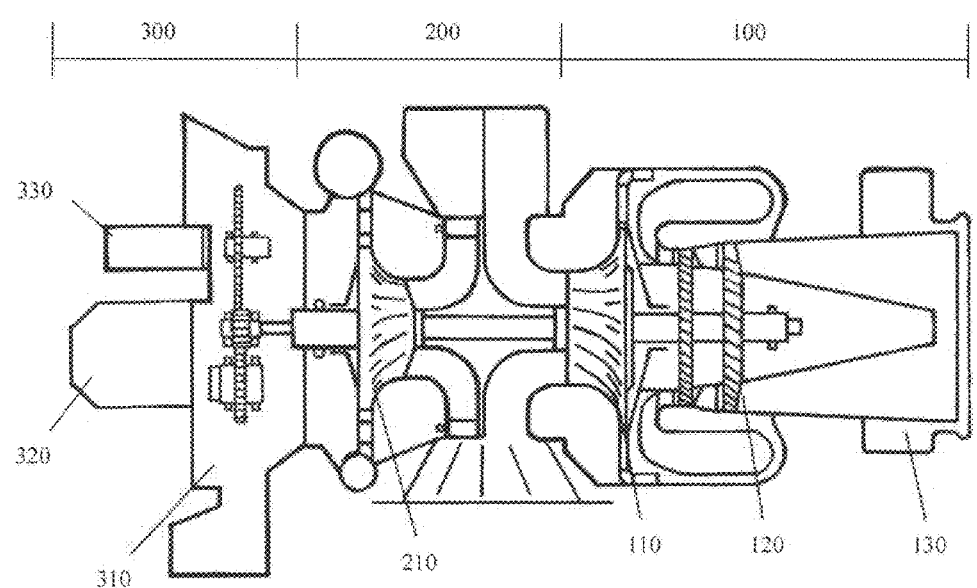
FIG. 1 is a schematic drawing illustrating the structure of the aircraft APU according to one example of the present invention.

Hereinafter, in order to give a dearer picture of the purposes, technical solutions and advantages of the embodiments of the present invention, the technical solutions in the embodiments of the present invention will be further described, taken in conjunction with the accompanying drawings in the embodiments of the present invention. Apparently, the described embodiments are only part of the invention rather than all embodiments. Based on the embodiments in the present invention, all other embodiments a person with ordinary skill in the art achieves without any creative effort shall fall within the protection scope of the present invention.

In the following detailed description, please refer to each drawing of the specification regarded as a portion of the application for illustrating the specific embodiment of the invention. In the drawings of the specification, similar reference signs describe substantially identical components in different schemas. Each specific example of the application are described with sufficient details in the following, in order to enable persons skilled in the art to embody the technical solution of the application. It should be understood that, other examples or modifications to the structure, logic or electrical characteristics of the examples of the application can also be used.

FIG. 1 is a schematic drawing illustrating the structure of the aircraft APU according to one example of the present invention. As shown in the FIG. 1, the aircraft APU mainly comprises power part 100, load part 200 and accessory part 300. Wherein, the power part 100 mainly comprises power yrs compressor 110, turbine component 120 and exhaust component 130. The load part 200 mainly comprises load compressor 210. The accessory part 300 mainly comprises, among others, accessory gear box 310, starter 320 and generator 330.

Figure 2:
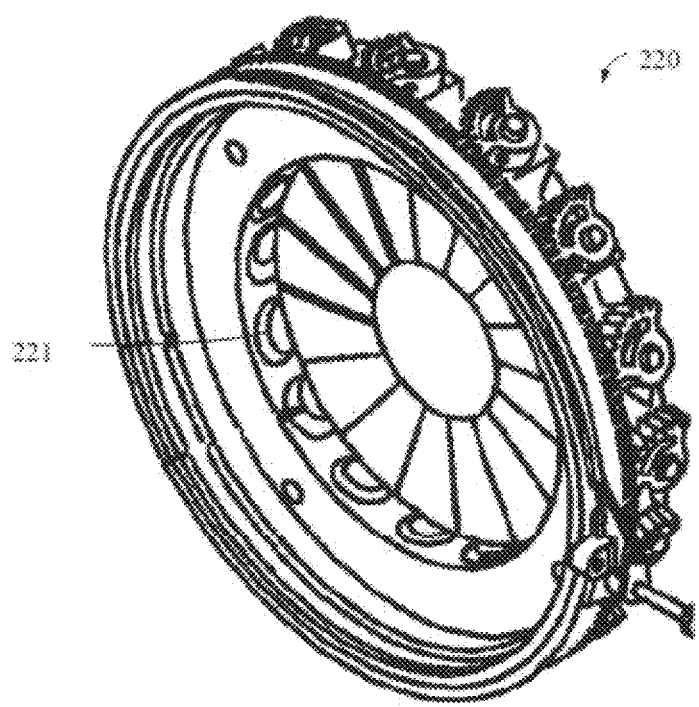
FIG. 2 is a schematic drawing illustrating structure of the inlet guide vane component according to one example of the present invention.

Referring FIGS. 1 and 2, the air stream entering from the inlet is divided into two streams. One enters into the power compressor 10 and turbine component 120, and is mainly used for driving the rotation of APU, and then the stream is exhausted through the exhaust component 130; the other stream enters into the load compressor 120, and this stream is pressurized by the load compressor, and mainly used for producing the compressed air for the engine of aircraft. Since the rotation speed of the APU rotator is constant, a flow control valve is positioned in the inlet of the stream, the valve is inlet guide vane IGV. IGV regulates the opening of the guide vane in real-time according to the actual need of air in the aircraft, and thereby control the air amount entering into the load compressor.

FIG. 2 is a schematic drawing illustrating structure of the inlet guide vane component 220 according to one example of the present invention. As shown in FIG. 2, the inlet guide vane component is substantially disc-shaped. A plurality of inlet guide vane IGV221 is positioned on the side close to the bottom of the disc. A plurality of inlet guide vane IGV can open with different angles under control, and thus regulate the flow of air entering the load compressor.

Figure 3:
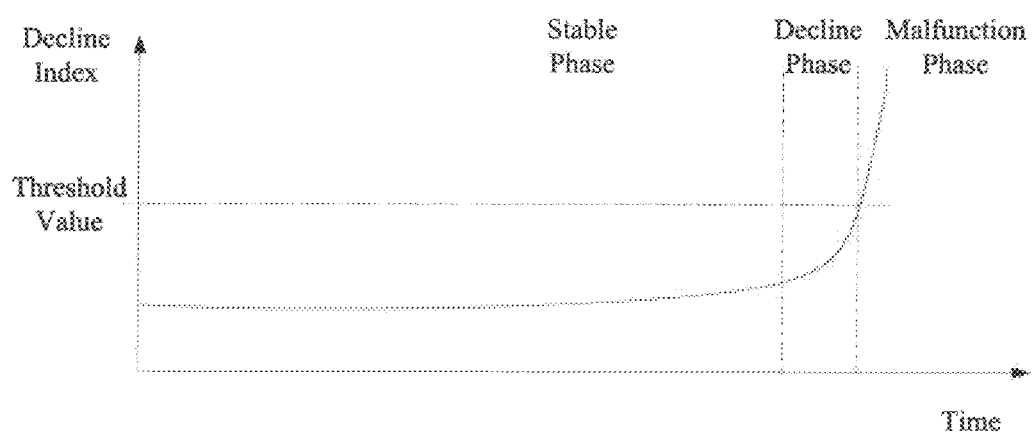
FIG. 3 is a curve diagram illustrating the change of the performance of APU caused by the turbine vane fracture and rotor shaft jam according to one example of the present invention.

FIG. 3 is a curve diagram illustrating the change of the performance of APU caused by the turbine vane fracture and rotor shaft jam according to one example of the present invention. It can be seen from FIG. 3 that: in the early and middle phases in use of APU, the turbine vane of APU is not deformed to stretch or crack, the performance of APU is stable and in stable phase. As the time goes by, because the performance of aircraft APU is gradually degenerated, the decline index is increase. In the late phase in use of APU, the turbine vane of APU becomes deformed to stretch and crack. This phenomenon demonstrates the performance of APU enters into the decline phase. When exceeding some threshold values, the performance of APU enters into the malfunction phase, and APU will encounter a malfunction at any time. When APU enters the malfunction phase, the use of APU is affected harmfully and adverse consequences will be brought to the quality of service and flying safety; moreover, non-planned maintenance tends to happen which causes the flight to delay and ground. Once the APU turbine enters into the decline phase, the decline index increases fast. Therefore, the monitoring of the APU turbine entering into the decline phase is of great importance.

There is no measure in the prior art to detect whether the performance of the APU comes into the decline phase due to the turbine vane fracture and rotor shaft jam. But such detection can be realized by some examples of the invention. The detection of decline phase has the following benefits: first, when APU is in decline phase, the probability of the occurrence of a failure is still very low. If the maintenance/repair is proceeded on the aircraft at this time, the flying safety and quality of service can be guaranteed; second, when detecting that the APU is in decline phase, the airline can arrange the maintenance/repair of the aircraft timely, and thus the non-planned maintenance can be avoided, the flight delay can be reduced accordingly, and therefore a waste of the cost for maintenance/repair resulted from the inspection in fixed period can be avoided at the same time. Of course, the example of the invention can also be applied for the inspection in malfunction phase.

In order to realize the monitoring of the malfunction of the turbine and rotor shaft jam of APU, it is needed to select the proper type of data for monitoring in a extremely numerous data monitored by aircraft. Since many types of monitoring data can be influenced by multiple factors, and the error message rate needs to be maintained in a relative low level to ensure the monitoring method acts effectively. Even for the professionals with years of experience, it is difficult to select the proper types of monitoring data.

According to one example of the invention, the malfunction of the APU turbine vane fracture and rotor shaft jam is determined by 3 operation parameters: start time STA, the highest exhaust gas temperature EGTP on start of APU and the NPA (Number of Proportion in APU) at the highest temperature, singly or in combination, wherein the definition of NPA is the percent of the rotation speed of the turbine when the exhaust temperature EGT of APU reaches its peak value in the start stage of APU with respect to the constant rotation speed in normal operation of APU (% RPM/APU RPM). NPA can reflect the vane efficiency of the turbine.

Since APU is a small turbine engine, the clearance dimension between the rotating components and the case largely influences the performance and efficiency of APU; wherein the clearance between the turbine and turbine casing is very important. If the clearance between the turbine and turbine casing is too large, too much gas is lost, and the APU efficiency becomes low. While the clearance between the turbine and turbine casing is too small, the scraping malfunction will easily occur. In general, the clearance between the turbine and turbine casing is very small.

The inventor of the application finds that, since the turbine vane affected by long-term thermal stress and centrifugal force, the erosion of turbine vane material and release of the turbine vane are apt to occur. The change of vane cause the rotator of the turbine to rotate unbalancedly, i.e., eccentric rotation, and as a result the turbine shaft will bend. Such bend is irreversible. The bend of the turbine shaft will lead to the scrub between the turbine vane and turbine casing, and finally the vane cracks. Once this case occurs, the situation will get worse with the time. The release of vane material will become fast, and the crack of vane will extend, the abrasion will spread.

Once the above phenomena occur, the vane fracture and the shaft bearing abrasion will occur after 300-400 flying hours, the metal shavings will appear and APU will shuts down automatically. The APU turbine vane fracture will cause the rotor shaft jam, and finally the internal injury of APU. The report after shut-down of APU will show over-temperature with trouble code 098, with information of FUEL CTL UNIT(8022KM), GEN SCAV FILTER (8069KM)/AND LUBE FILTER(8076KM). The metal shavings will be found in further examination, lubricant filter 8076KM pressure difference indicator leaps out, starter motor abrasion indicator leaps out, and abnormal noise occurs when APU starts. But it is too late, the flight delay and emergency repair is inevitable, and the cost for repair will be expensive necessarily.

When the turbine rotates at high speed in high temperature, the turbine shaft will bend as a result of the thermal stress and centrifugal force, and resulting the scraping between the turbine vane and the turbine casing. When the scraping occurs, the efficiency of APU will decrease, and the start time STA will change. As a result of the influence of scraping, the start time STA will become longer, and a top point appear among the monitoring data of STA.

However, the degeneration process of the bend of the APU turbine shaft is relatively long. Do not want to be limited with the theory, the inventor notes that, at 50☐ under zero to 600☐ of external temperature, the different expansion coefficients of the turbine vane and turbine casing will cause the clearance between the turbine vane and turbine casing to change with the changes of the external temperature. When the external temperature gets higher, the clearance between the turbine vane and turbine casing will get smaller, and when the external temperature gets lower, the clearance between the turbine vane and turbine casing will get larger. With the changes of the external temperature, the start time STA will return into the range of normal value with a time period. Then, since the loss of turbine vane material will cause the aggravated bend of turbine shaft, and the probability of the scraping between the turbine vane and turbine casing will increase gradually. The raise of the external temperature also has some effect. The start time STA will reach a top point and become discrete. Since the start time STA is very stable generally, the regular pattern of the change of the start time STA on a long period, that is, top point appearance-returning to normal-top point appearance once again and discrete, is a feature of the malfunction of the APU turbine vane fracture and rotor shaft jam.

At the same time, in the above process, the efficiency of the burning of fuel will decrease accordingly. Since the rotation speed of APU is constant on operation, the burning efficiency must be increased in order to input the same torque, that is, the power loss caused by the low efficiency will be made up by increasing the supply of fuel oil. However, the reduce of efficiency will lead to the increase of waste heat, that is, the circumstance that the consumption of fuel oil increases while the input power remains unchanged will happen. The excess heat will go into the atmosphere with the exhausted gas, causing the increase of the temperature of the exhausted gas. Therefore, the highest exhaust gas temperature EGTP on start of APU will increase gradually with the decrease of pneumatic efficiency of the turbine vane, till it reaches the protected temperature of the exhausted gas (i.e. redline value, about 850° C.).

To the parameter NPA, the efficiency of turbine will be reduced by the bend of turbine shaft, the erosion and release of the vane and the injury caused by scrubbing. NPA will decrease gradually with the decline of the pneumatic efficiency of the turbine vane.

According to one example of the invention, the standard deviation of the temperature of the exhausted gas EGT, NPA and STA can used as the effective parameters for judging the APU turbine vane fracture and rotor shaft jam sometimes. According to one example of the invention, when the circumstances of APU turbine vane fracture and rotor shaft jam occurs, the standard deviation of EGT and NPA increase 30-50%.

Generally, when the APU turbine vane fracture and rotor shaft jam occurs, the EGT is close to the red line value, IGV is increase to reduce the load, and STA value becomes discrete as a result of the instability of STA caused by the unbalance of the turbine shaft. Wherein, the EGT redline value reflects the limiting value in APU operation. For example, as for APU of GTCP131-9A type, the redline value of EGT is 640, and after 50 degrees revise of sea level, the redline of EGT is 690, the standard deviation of STA is 4 and NAP is 40. As for APU of APS3200 type, the redline value of EGT is 645, and after 50 degrees revise of sea level, the redline of EGT is 680, the standard deviation of STA is 10 and NAP is 32.

Further, when the temperature of the exhausted gas reaches the redline value, it is not allowed to further increase according the control strategy of APU. Under this circumstance, to make sure that the rotation speed of APU unchanged, the torque output must be reduced, that is, reducing the load. As described above, the air flow entering into the load compressor is regulated by different opening angle of the inlet guide vane IGV. Therefore, APU will increase the angle of the inlet guide vane IGV, and reduce the air flow entering into the load compressor, and thus reduce the bleed air supply to the main engine. Therefore, the angle of the inlet guide vane IGV will change correspondingly. As such, as one example of the invention, the angle of IGV can represent the performance of APU. GTCP131-9A, the IGV redline is 85 degrees, and the IGV redline of APS3200 is 15 degrees.

In some special cases, when the circumstances of APU turbine vane fracture and rotor shaft jam is to occur, the EGT can decline but it will be more dangerous. Once this case occurs, the turbine vane may have displaced or extended, which causes the space between the turbine vane and casing becomes small, the efficiency of turbine thereby raises. However, the turbine vane will be likely to scrub with the casing and lead to the fracture of the vane. At this time, APU will not be overtemperature, instead, the temperature EGT decreases. Since impaired turbine only lasts for a short time period, for example about 200 hours, the fracture of turbine vane is most likely to occur in APU, and causing the serious injury of APU, the rotation shaft jam, and shut-down finally.

Therefore, among many APU-related data, the start time STA, the highest exhaust gas temperature on start EGTP, NPA, the revised value of the exhausted temperature EGT and IGV are selected to realize the monitoring for the malfunction of the APU turbine vane fracture and rotor shaft jam.

The APU operation parameters such as the start time STA, the highest exhaust gas temperature on start EGTP, NPA, the revised value of the exhausted temperature EGT and IGV can be acquired by various methods. For example, the above data can be acquired from the data stored in black box of the airplane and digital flight data interface unit DFDIU.

The above data can also be acquired by the data system supplied by the airplane makers and the real-time monitoring of the ground can also be realized. For example, the Aircraft Condition Monitoring System (ACMS) of Airbus and the Aircraft Heath Monitor (AHM) system of Boeing can both realize the monitoring of the operation data of the aircrafts. Moreover, once certain trigger conditions are meted, the message comprising a series of data information will be generated automatically.

According to one example of the invention, the related operation data of APU can be acquired by the aircraft data system (such as ACMS or AHM systems) and embodied in the generated relevant messages. Moreover, this kind of message information can be transferred to the ground by Aircraft. Communications Addressing and Reporting System (AGARS), and further distributed to the servers of different airlines. According to one embodiment of the invention, APU message can also be transferred by the communicating device or system of Aviation Telecommunication Network (ATN). Of course, the mode of message transfer can avoid the high cost and human failure caused by manual mode.

According to one example of the invention, the monitoring for the malfunction of the APU turbine vane fracture and rotor shaft jam can be realized by the data monitored by the APU-related messages. For example, the A13 message of Airbus, i.e. APU MES/IDLE REPORT, or the APU message of Boeing is just the case. In the following examples, it is illustrated by taking the A13 message of Airbus as an example. The treatment of APU message of Boeing is similar to this method.

FIG. 4 is drawing illustrating an example of the A13 message of Airbus. As shown in the figure, A13 message mainly comprises 4 parts of information, which are: the message heading, APU record information, the operation parameters in starting of the aircraft engine and the start parameter of APU.

The message heading is consisted of CC and C1 fields, and mainly includes the flight information of the aircraft, the segment wherein the is message generated, the state of bleed valves, total air temperature (i.e. the outer temperature) and the like information. The APU record information is consisted of E1 field, comprising APU serial number, operation time and cycle and other information. The operation parameters in starting of the aircraft engine is consisted of N1 to S3 fields; wherein N1 and S1 represent the operation on the time of starting the first aircraft engine, N2 and S2 represent the operation on the time of starting the second aircraft engine, and N3 and S3 represent the slow-down state of APU after completing the starting of engine by APU.

It can be seen from FIG. 4 that, the APU operation parameters such as the start time STA, the highest exhaust gas temperature on start EGTP, the angle of inlet guide vane IGV and peak EGT rotation are all included in the existed A13 message. Therefore, the data acquired by the message can realize the monitoring of the malfunction of the APU turbine vane fracture and rotor shaft jam.

Figure 5:
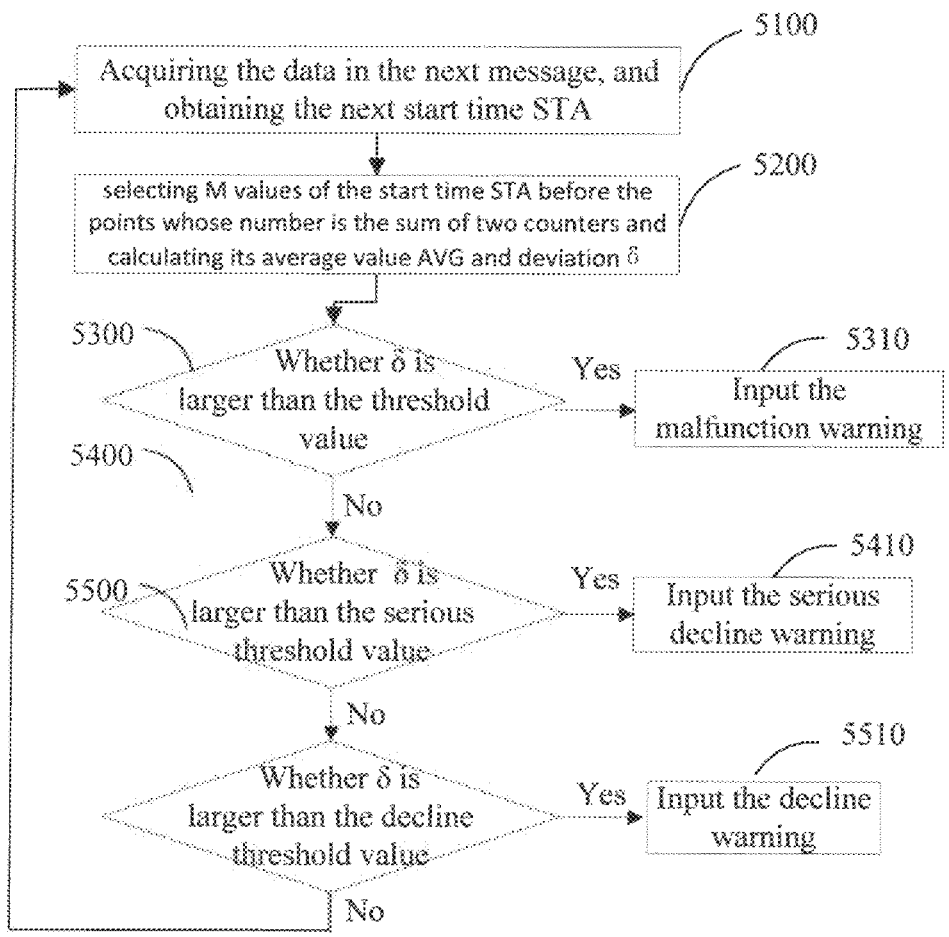
FIG. 5 is a flow diagram illustrating the method for monitoring the APU turbine and rotor shaft jam according to one example of the present invention.

FIG. 5 is a flow diagram illustrating the method for monitoring the APU turbine and rotor shaft jam according to one example of the present invention. In the example of FIG. 5, only start time STA is used. As shown in FIG. 5, in the method for monitoring the malfunction of the APU turbine vane fracture and rotor shaft jam 5000, in step 5100, acquiring the operation data of aircraft APU within a time period, which comprises but is not limited to the start time STA.

According to one example of the invention, the message in step 5100 can be acquired from the APU message. For example, the control centre of Society International De Telecommunication Aeronautiques (SITA) and the control centre of Aviation Data Communication Corporation (ADCC) can obtain the message of the operation of the APU remotely in real-time, and decode the message of the APU operation modes by message decoder, and achieve the desired operation information of the aircraft APU.

In step 5200, calculating the average value AVG and deviation δ within the time period. In step 5300, judging whether the deviation δ obtained in step 5200 exceeds the failure threshold value. If exceeding the failure threshold value, input the failure warning in step 5310.

When the judgment in step 5300 is no, comparing whether the deviation δ obtained in step 5200 exceeds the serious decline threshold value in step 5400. If exceeding the serious decline threshold value, input the serious decline warning in step 5410.

When the judgment in step 5400 is no, comparing whether the deviation δ obtained in step 5200 exceeds the serious decline threshold value in step 5500. If exceeding the serious decline threshold value, input the serious decline warning in step 5510.

As for different APU, the value of each threshold is a little different. According to one example of the invention, the fluctuation when the APU of one type is in stable phase can be obtained, and the threshold values in other phases can be further estimated based on the fluctuation in stable phase as a standard. For example, according to one example of the invention, the decline threshold value is about 2 times of the fluctuation rate in stable phase, the serious decline threshold value is about 4 times of the fluctuation rate in stable phase, and the failure threshold value is about 6 times of the fluctuation rate in stable phase.

Through the above methods, it can be judged that whether the start time STA of APU within the time period becomes discrete, and thus realizing the monitoring for the malfunction of the APU turbine vane fracture and rotor shaft jam.

When the new APU operation data is generated, repeating the method 5000 for monitoring the malfunction of the APU turbine vane fracture and rotor shaft jam by the new generated APU operation data with the time period unchanged, thus the real-time monitoring for the malfunction of the APU turbine vane fracture and rotor shaft jam can be realized.

The method for analyzing the change trend by the updating data within a fixed time period can be called scrolled window method. The size of scrolled window, i.e. the number M of points included within the range of calculating, depends on multiple factors, such as, the time interval of measurement, the control strategy and others. If the size is too small, the change of fluctuation is more easily influenced by the normal fluctuation, and more error messages will be generated, the effect of the invention will be affected finally. If the size is too large, although the change trend is still correct, this can decrease the timeliness of the invention, causing the warning information cannot be sent out timely. Therefore, the size of the scrolled window has an important effect on the invention. According to one example in the invention, the value of M is about 30 in case of measuring 2-3 points daily. According to another example in the invention, the value of M is about 20 in case of measuring no more than 2 point(s) daily.

According to one example of the invention, if the intensive warnings occur in a time period, and returning to normal, then intensive warnings repeat, and returning to normal again, it can be judged that the malfunction of the APU turbine vane fracture and rotor shaft jam occurs. The said intensive warnings comprise continuous warnings over 3 times or warnings with interval less than a warning.

According to one example of the invention, determining whether the change trend of the previous STA data appears a process of gradual raise and then returning to normal according to the history data of the start time STA. According to one example of the invention, the history data of STA in half of a year is obtained. According to one example of the invention, the history data of STA in one year is obtained.

Figure 6:
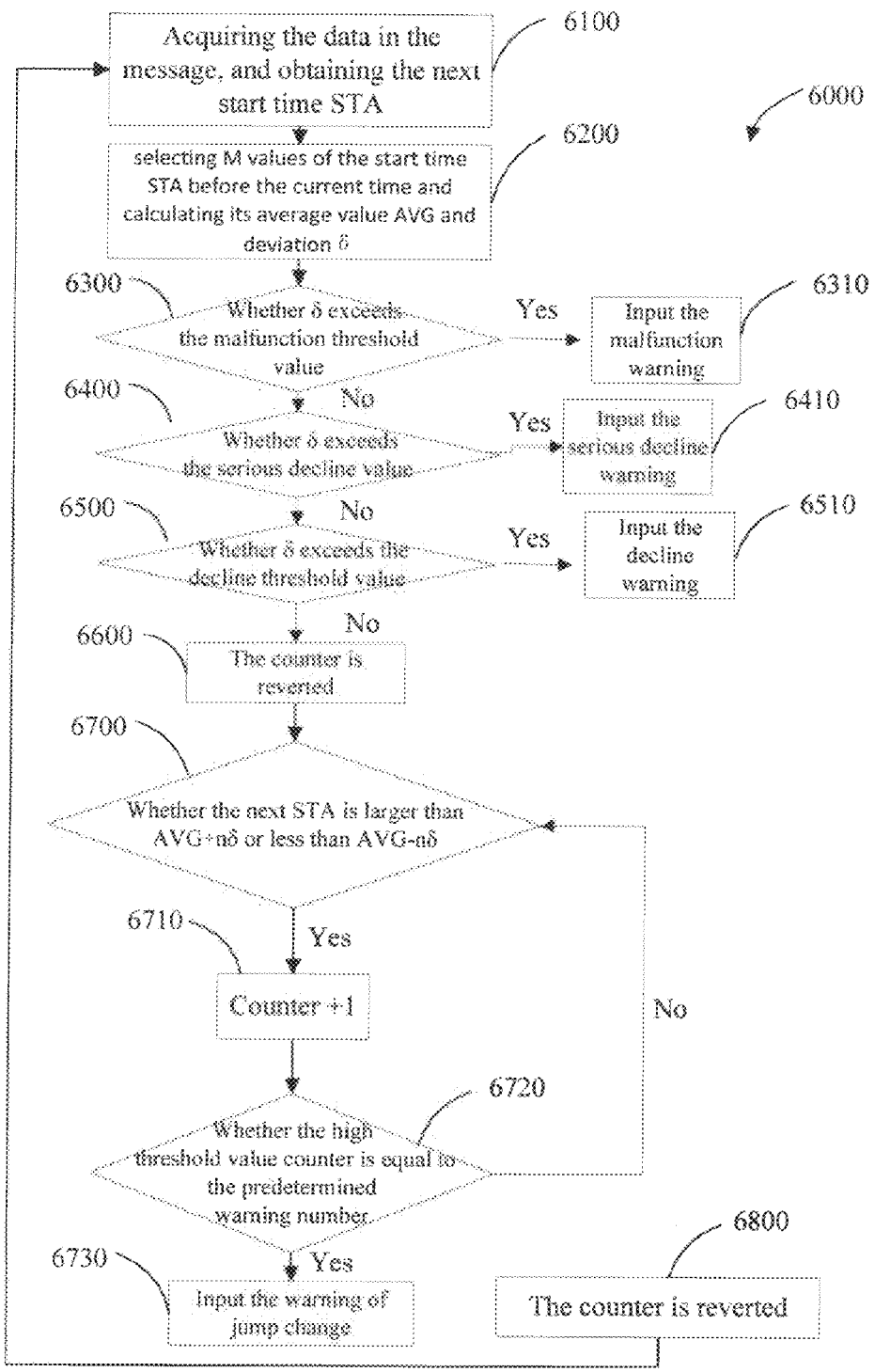
FIG. 6 is a flow diagram illustrating the method for monitoring the APU turbine and rotor shaft jam according to another example of the present invention.

FIG. 6 is a flow diagram illustrating the method for monitoring the APU turbine and rotor shaft jam according to another example of the present invention. In the example of FIG. 6, only one parameter of start time STA is utilized. The difference between FIGS. 6 and 5 is the algorithm for STA discrete degree. By the method of FIG. 6, the discrete change of STA can be found quickly, but error message is apt to occur. The methods of the examples in FIGS. 5 and 6 can be used in combination.

As shown in the figure, the method 6000 for monitoring the malfunction of the APU turbine vane fracture and rotor shaft jam, in step 6100, the method is performed by acquiring the operation data at some working time of aircraft APU, such as the start time STA, which is similar to the example shown in FIG. 5.

According to one example of the invention, the desired information in step 6100 can be acquired by similar mode as step 5100.

In step 6200, selecting M values of the start time STA before the current time and calculating its average value AVG and deviation δ. Calculation of the average value and deviation of a certain number of the previous points is to set a variation range for the next point which may be noise needs to be removed. According to the following description, one counter is used for recording the deviation point which changes beyond the preset range. When the number of times the deviation points appear continuously do not reach the number of warning, these deviation points are not counted into the range of samples calculating the average value and standard deviation. According to one example of the invention, the value of M can be 20.

In step 6300, comparing whether the deviation δ obtained in the previous step exceeds the failure threshold value. If exceeding the failure threshold value, issuing the failure warning in step 6310.

When the judgment in step 6300 is no, entering step 6400, comparing whether the deviation δ obtained in step 6200 exceeds the serious decline threshold value in step 6400. If exceeding the serious decline threshold value, input the serious decline warning in step 6410.

When the judgment in step 6400 is no, entering step 6500, comparing whether the deviation δ obtained in step 6200 exceeds the serious decline threshold value in step 6500. If exceeding the serious decline threshold value, input the serious decline warning in step 6510.

When the judgment in step 6500 is no, entering step 6600, setting the counter to zero. This because that the deviation point is disconnected through the previous judgment. In order to calculating the number of the continuous deviation points, it is needed to set the counter to zero and recount.

In step 6700, judging whether the start time STA corresponding to the next data point is greater than AVG+nδ or less than AVG−nδ, wherein the value of n is determined by control strategy. If the value of n is high, the control of sudden-change points is looser, and error message can be reduced in this way, but the risk of failing to inform may exist; if the value of n is low, the control of sudden-change points is stricter, and the risk of failure can be avoided, but frequent warning might occur. Generally speaking, the value of n is between 1-5. According to one example of the invention, the value of n is 3.

If the judgment in step 6700 is yes, entering step 6710, the counter +1. In the next step, step 6720, judging whether the high threshold value counter is equal to the preset warning number Z. If the judgment is no, returning step 6700. If the judgment is yes, it demonstrates that the start time STA continuously reaches the preset warning number Z which exceeds the preset normal variation range and the temperature jumps upward. At this time, entering step 6730 and issuing the warning of jump change.

According to one example of the invention, since a single temperature jump may be caused by various reasons, warning signal can be output under the condition that a certain numbers being exceeded, to exclude the error message. The value of the preset warning number Z is related to control strategy, and is generally 2-5.

In step 6800, the counter is reverted to zero. This because that, if the number of continuously deviated points reaches the preset warning number, the occurrence of deviation points is not occasional, and the continuously deviated points cannot be excluded as noise. At this time, the counter is reverted to zero, and theses deviation points will be retained when entering into step 6200 in the next cycle, and will be taken into calculation. When this step is finished, returning to step 6100.

According to one example of the invention, determining whether the change trend of the previous STA data appears a process of gradual raise and then returning to normal according to the history data of the start time STA. According to one example of the invention, acquiring the history data of STA in half of a year or in one year is obtained.

Figure 7:
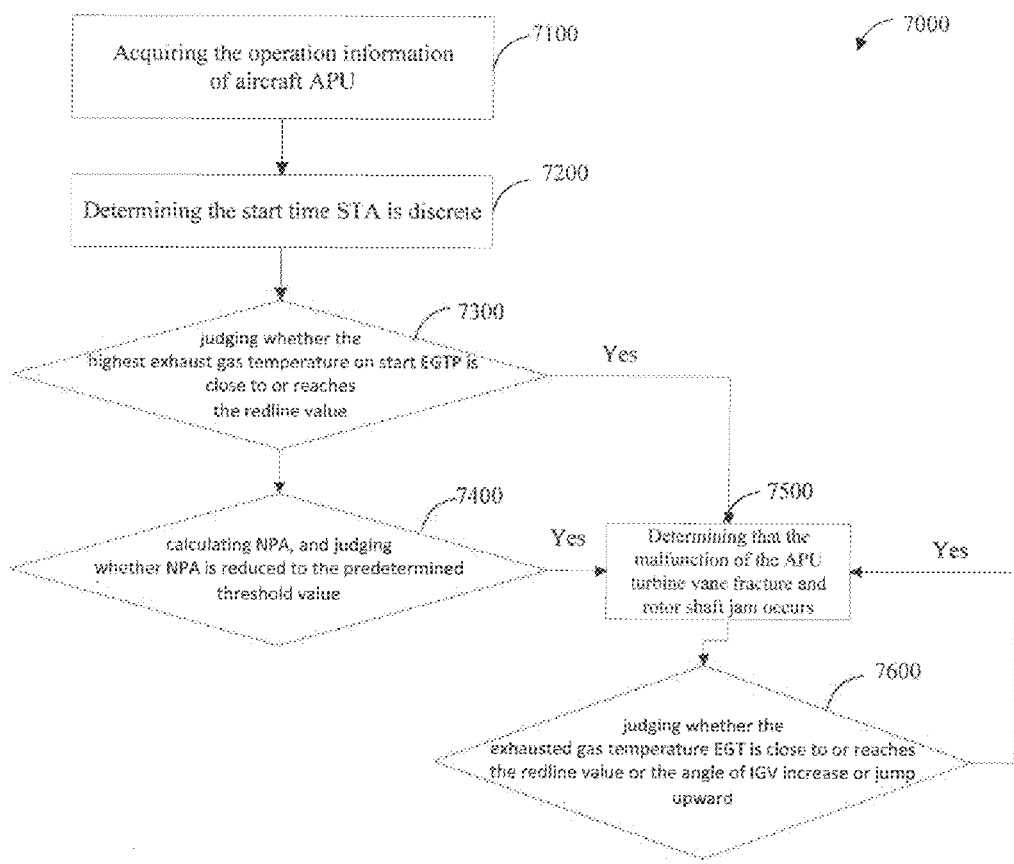
FIG. 7 is a flow diagram illustrating the method for monitoring the APU turbine and rotor shaft jam according to yet another example of the present invention.
Figure 8A:
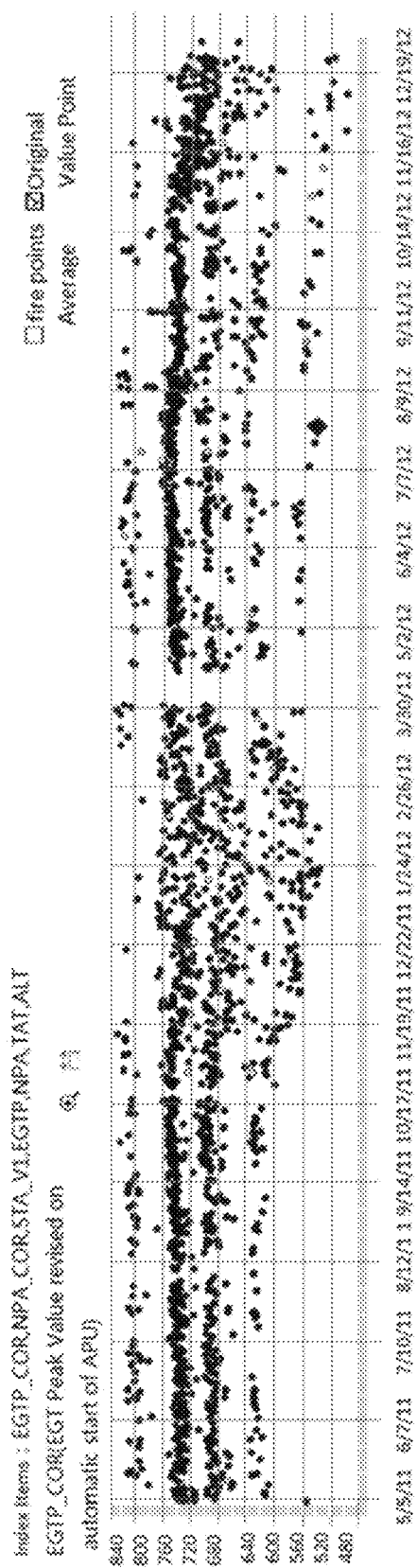
FIGS. 8A-8G are a statistical data diagram recorded at the time of the APU turbine and rotor shaft jam according to one example of the present invention.
Figure 8B:
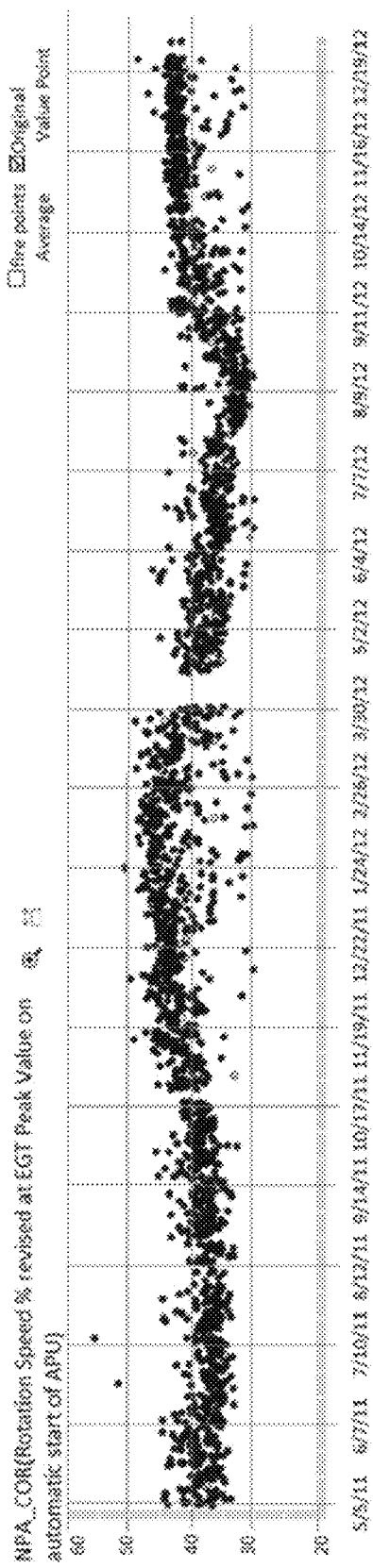
Figure 8C:
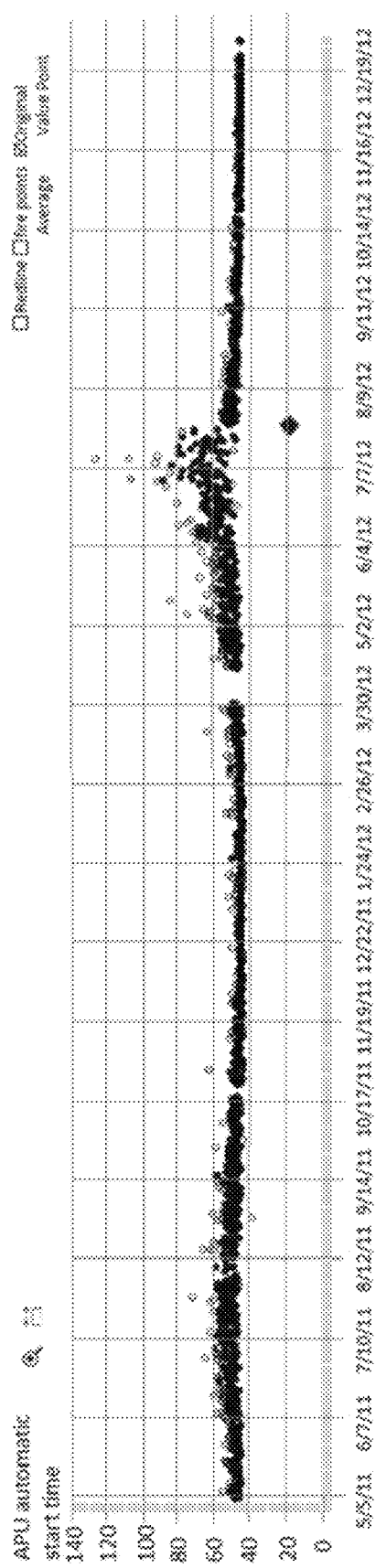
Figure 8D:
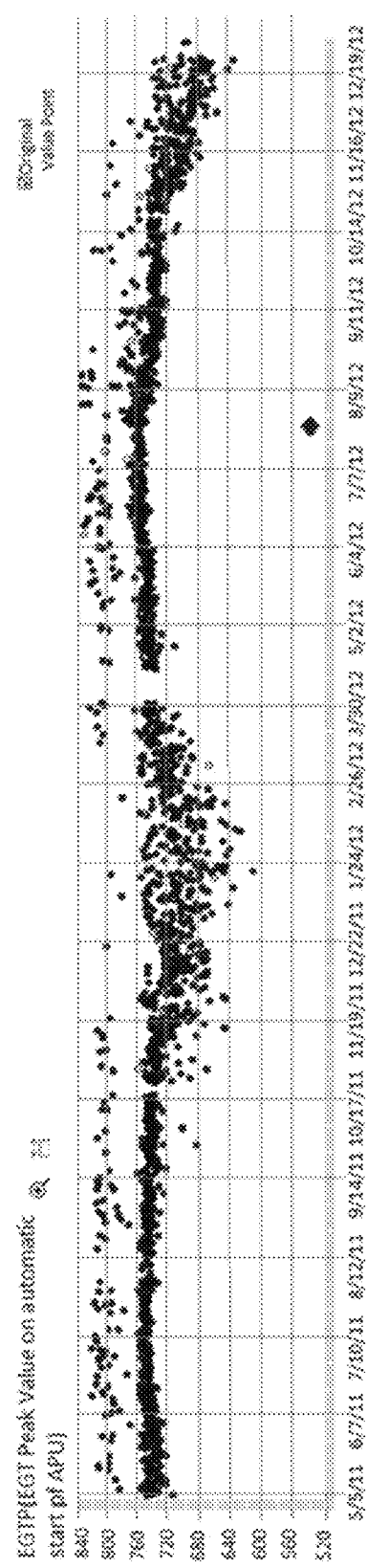
Figure 8E:
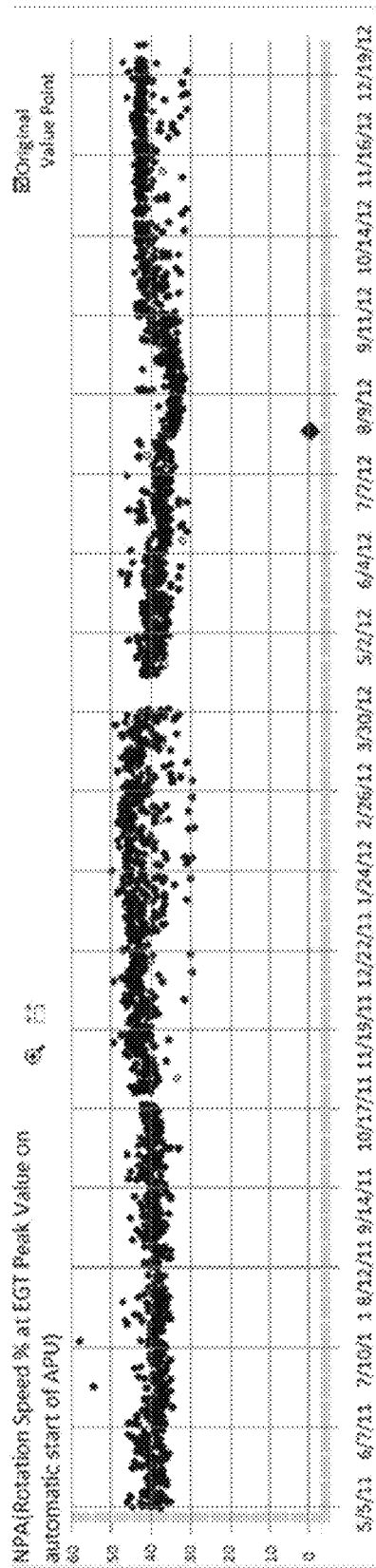
Figure 8F:
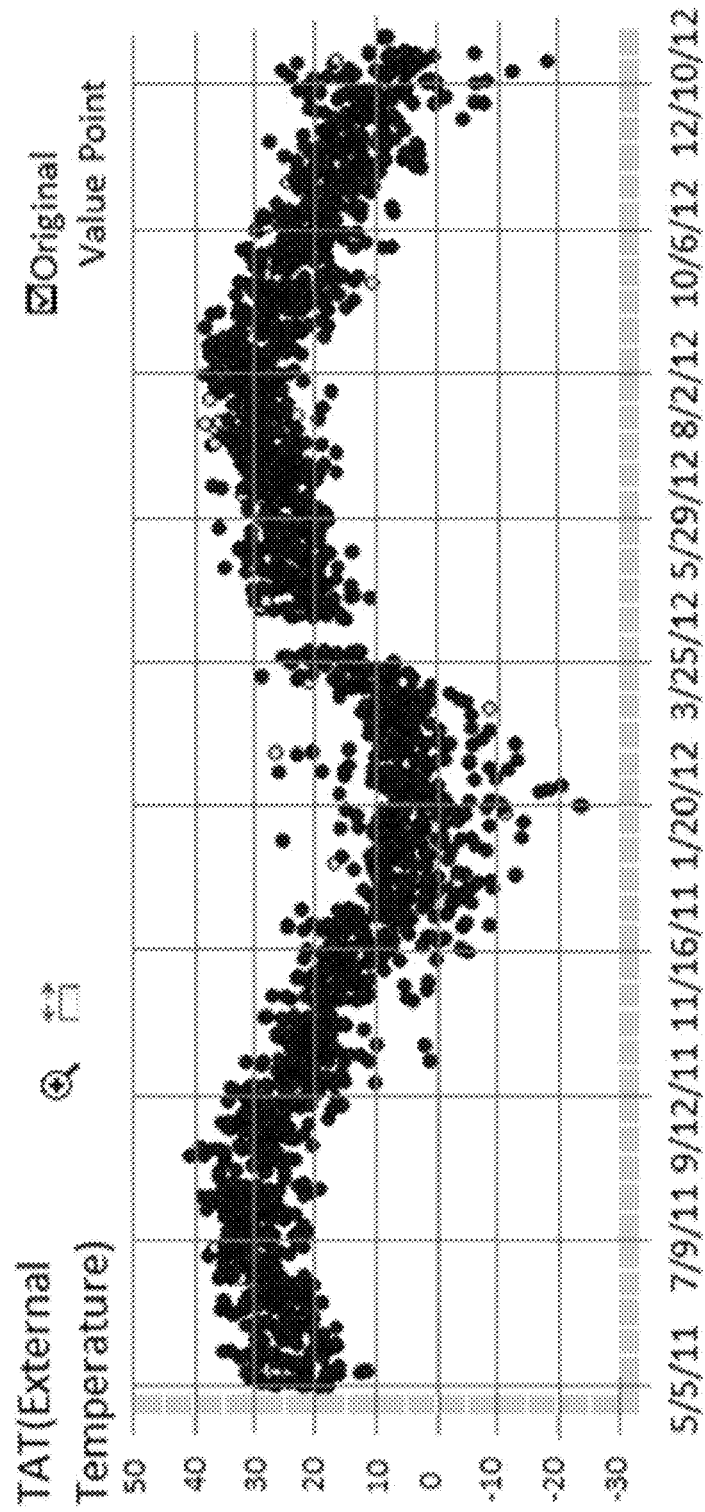
Figure 8G:
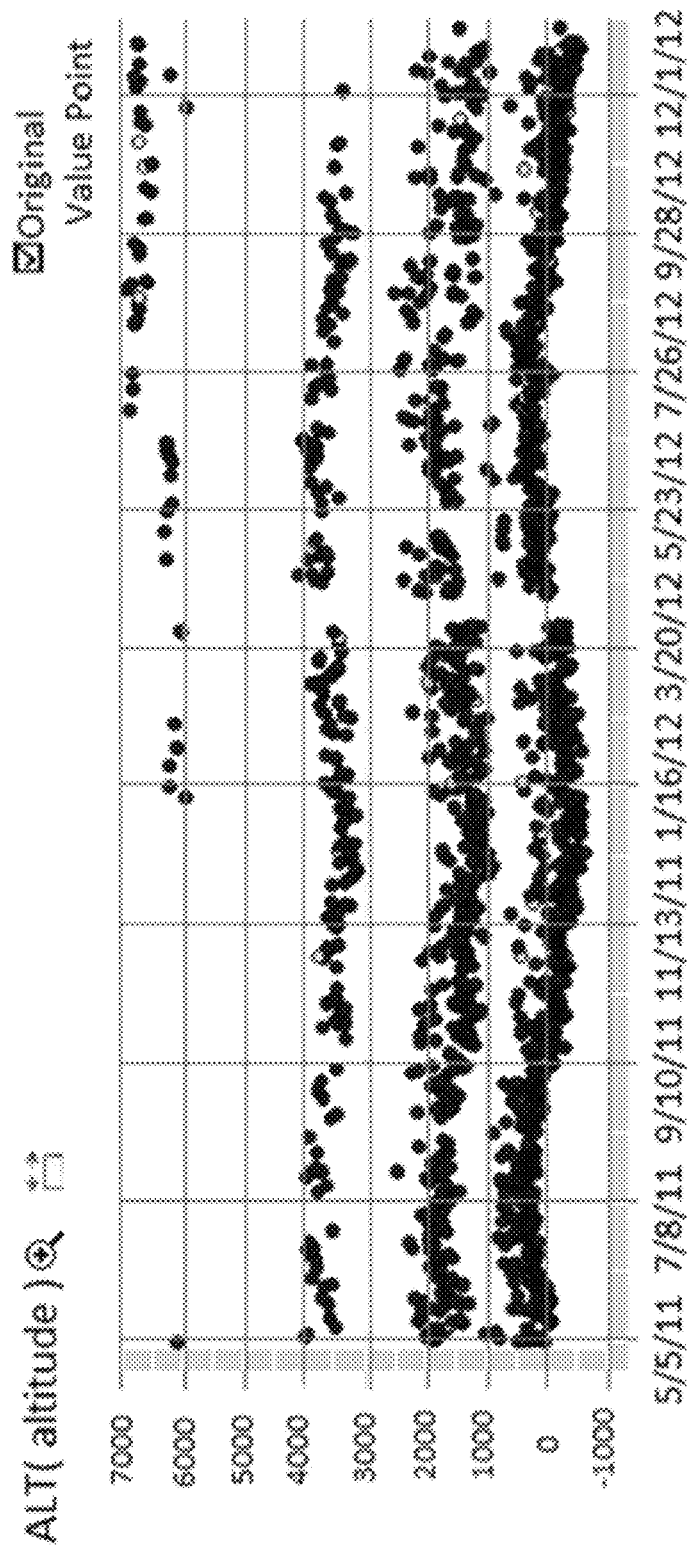
Figure 9A:
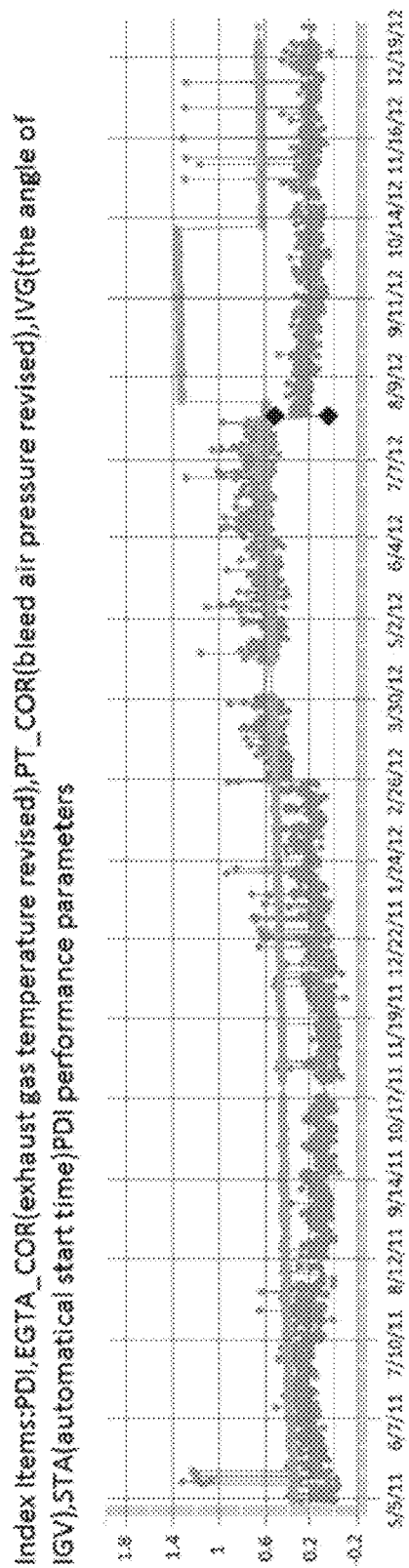
FIGS. 9A-9E are a statistical data diagram of other operation parameters of APU in the example illustrated in FIG. 8.
Figure 9B:
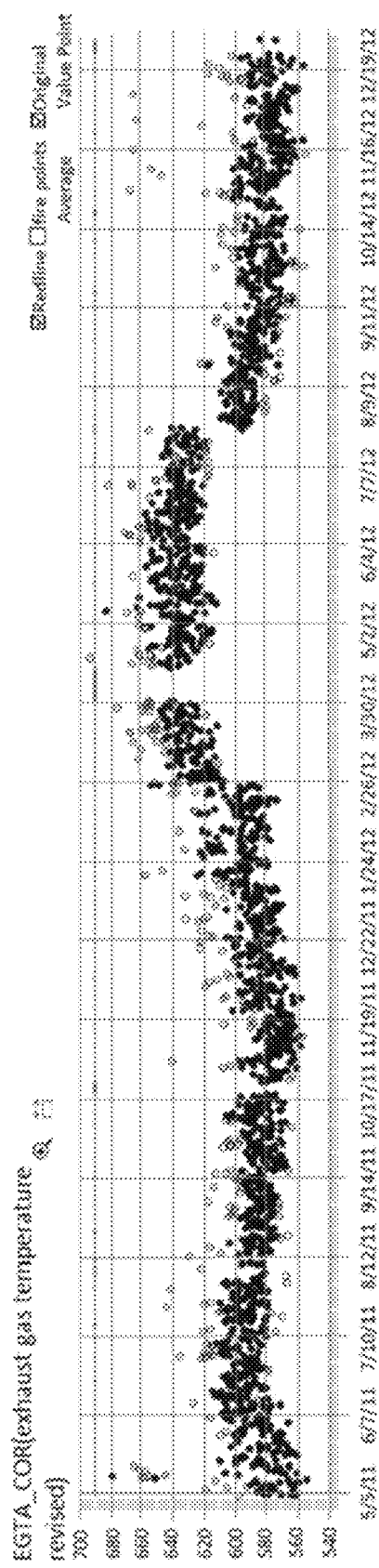
Figure 9C:
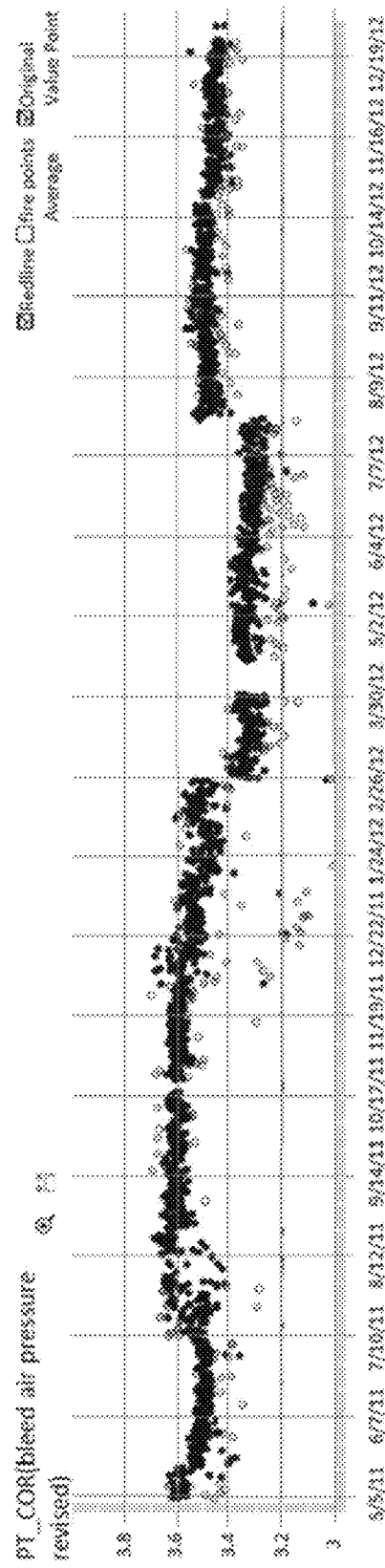
Figure 9D:
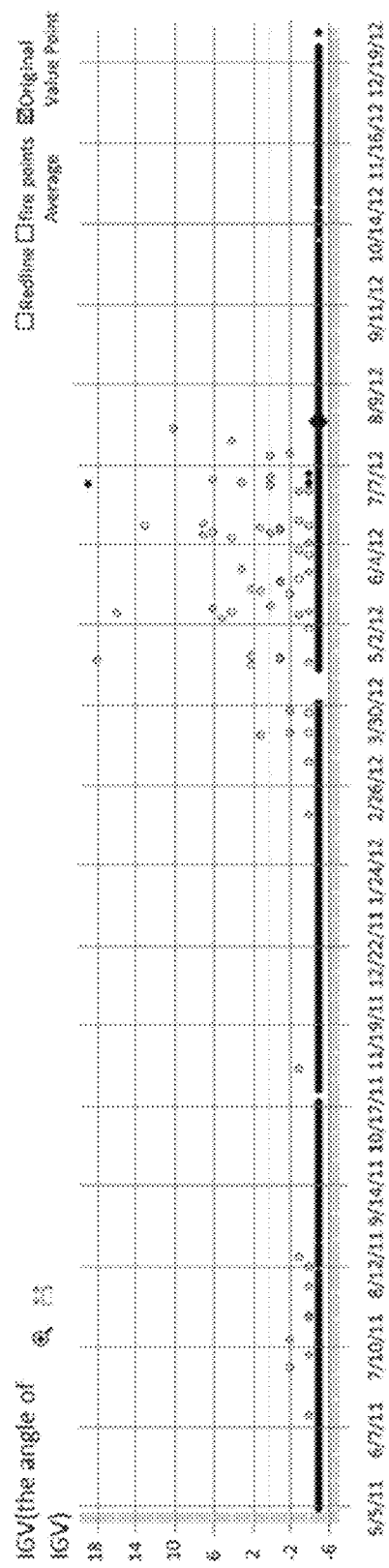
Figure 9E:
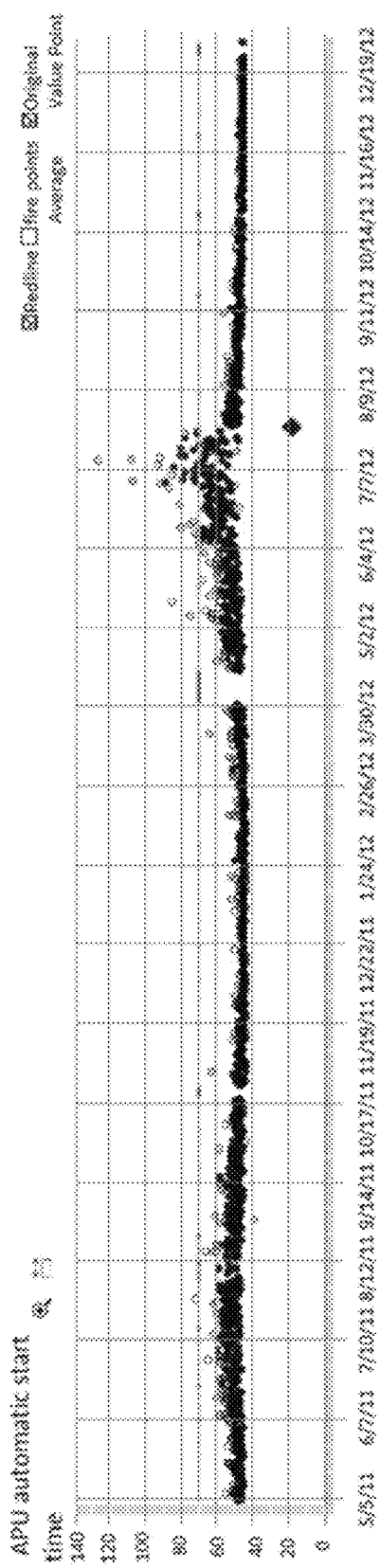
Figure 10A:
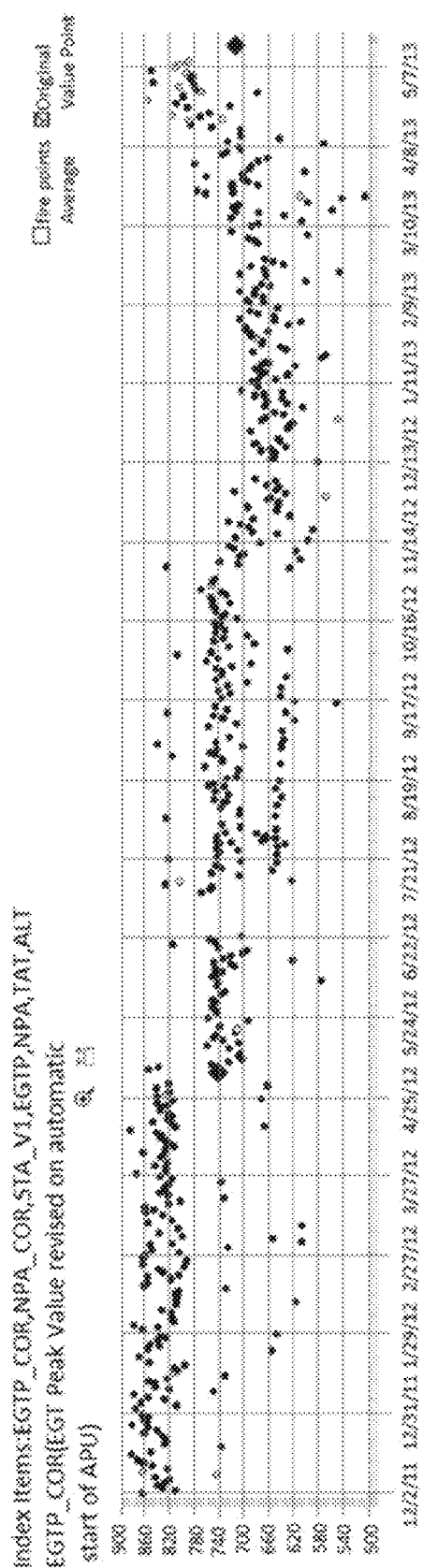
FIGS. 10A-10G are is a statistical data diagram recorded at the time of the malfunction of the turbine vane fracture and casing jam according to one example of the present invention.
Figure 10B:
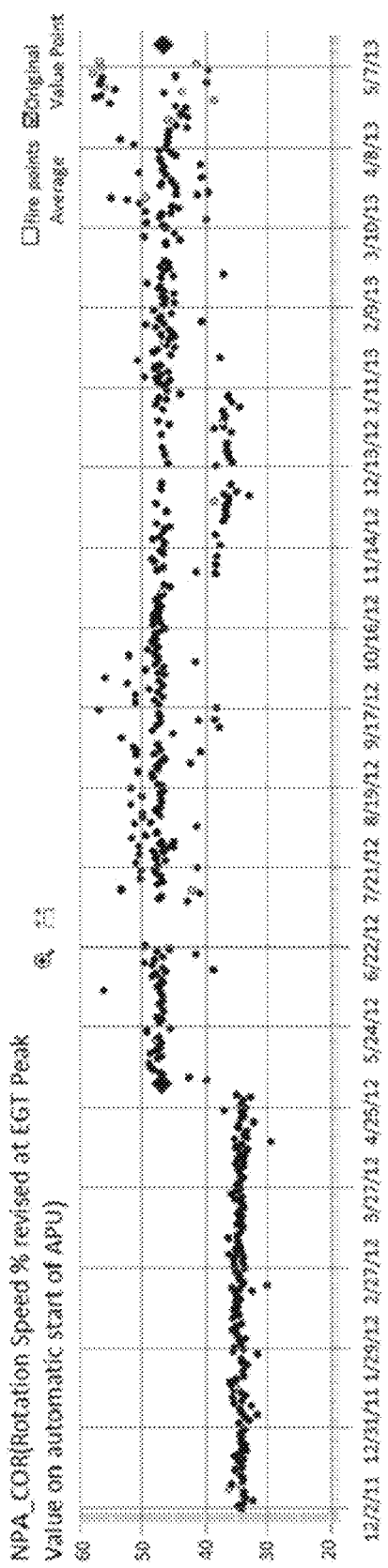
Figure 10C:
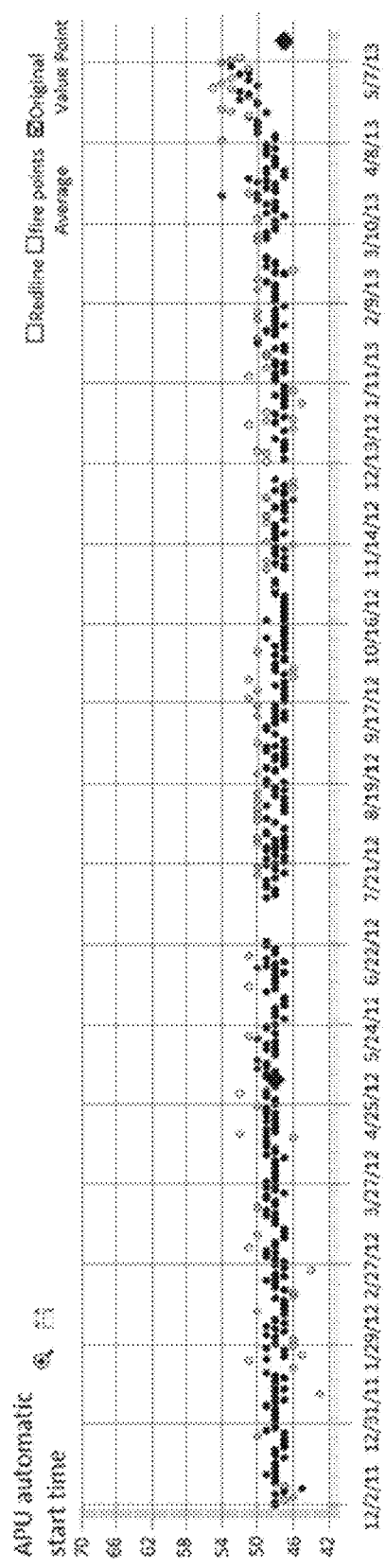
Figure 10D:
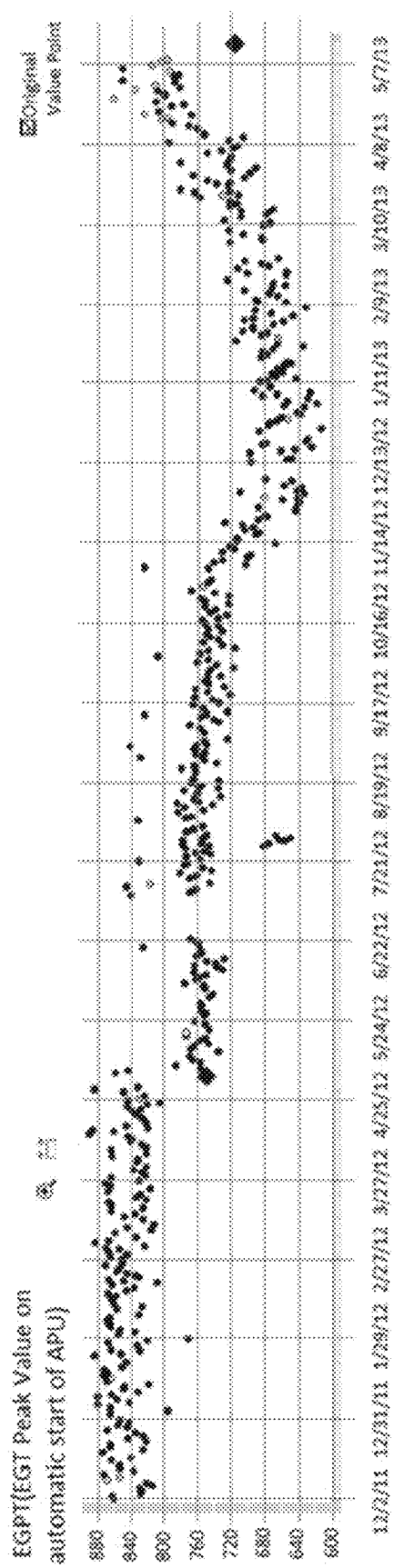
Figure 10E:
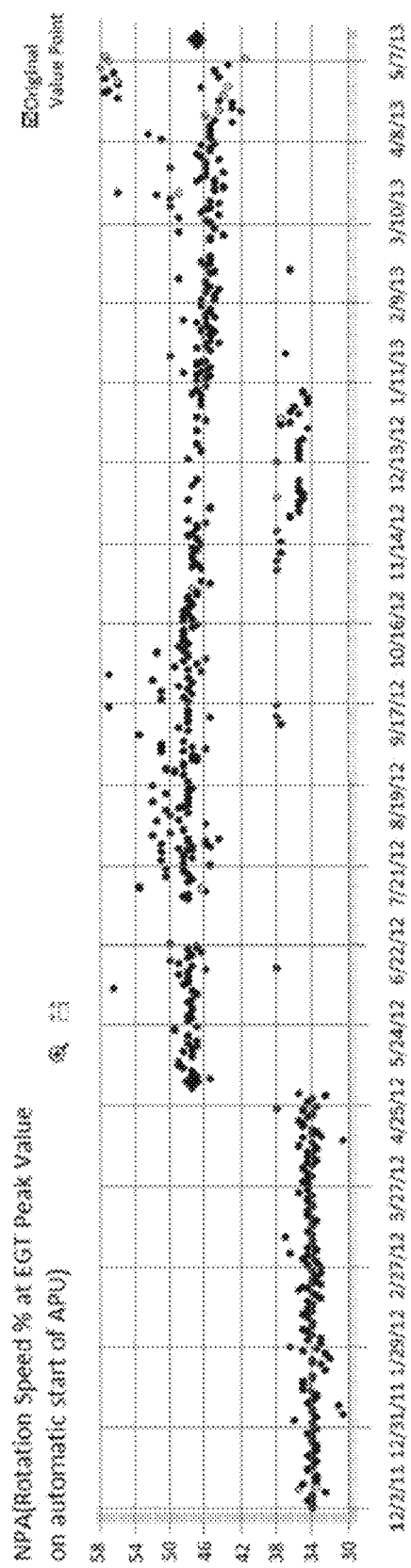
Figure 10F:
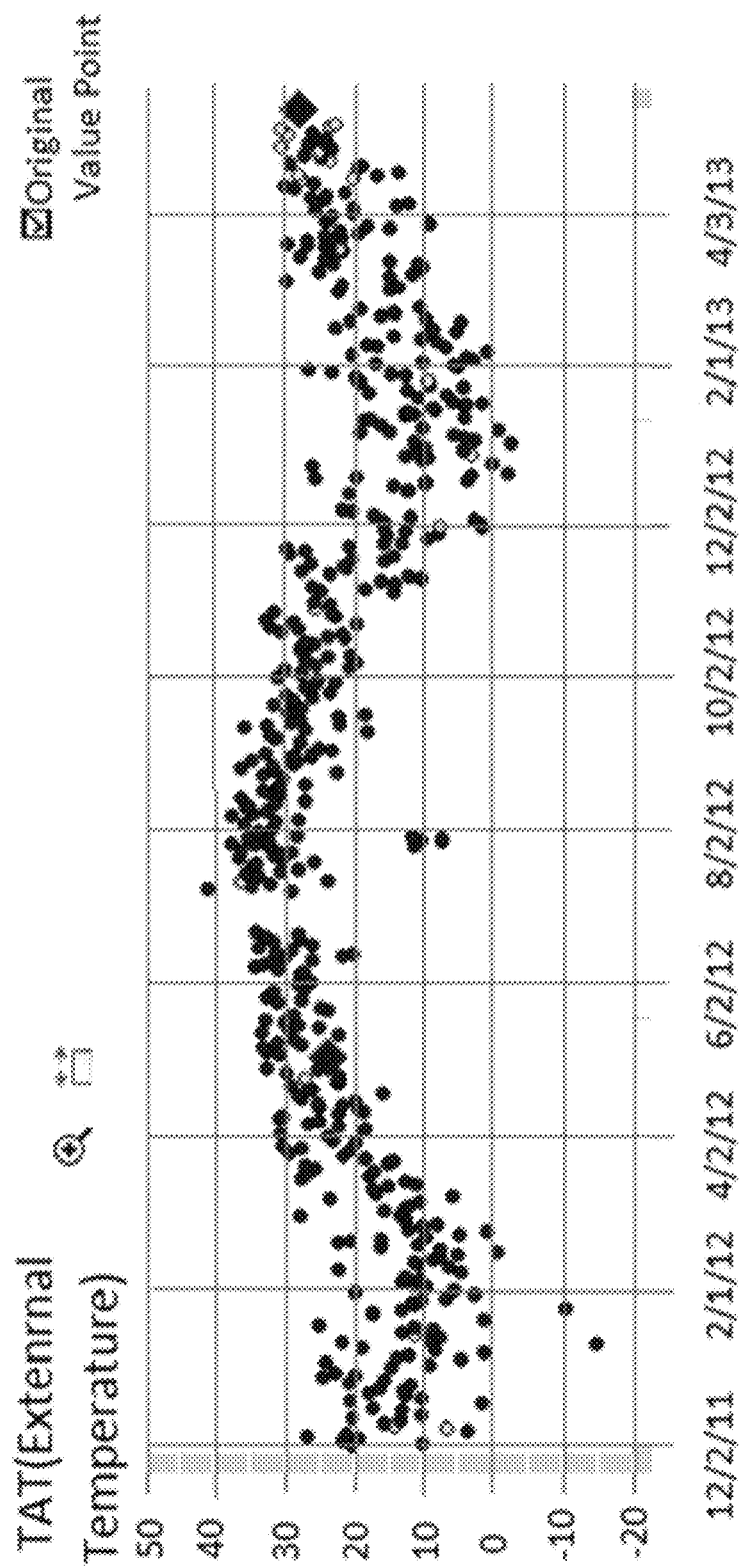
Figure 10G:
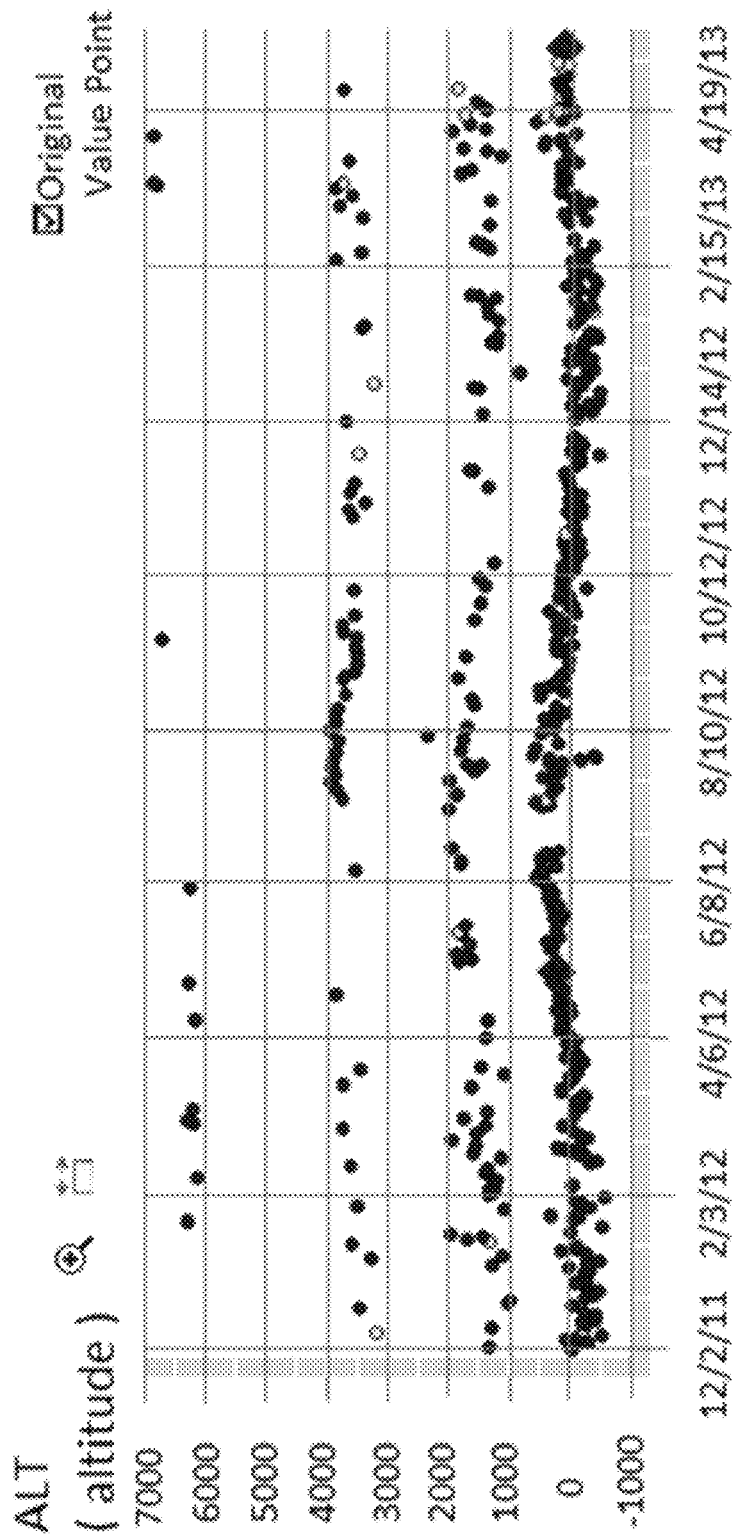
Figure 11A:
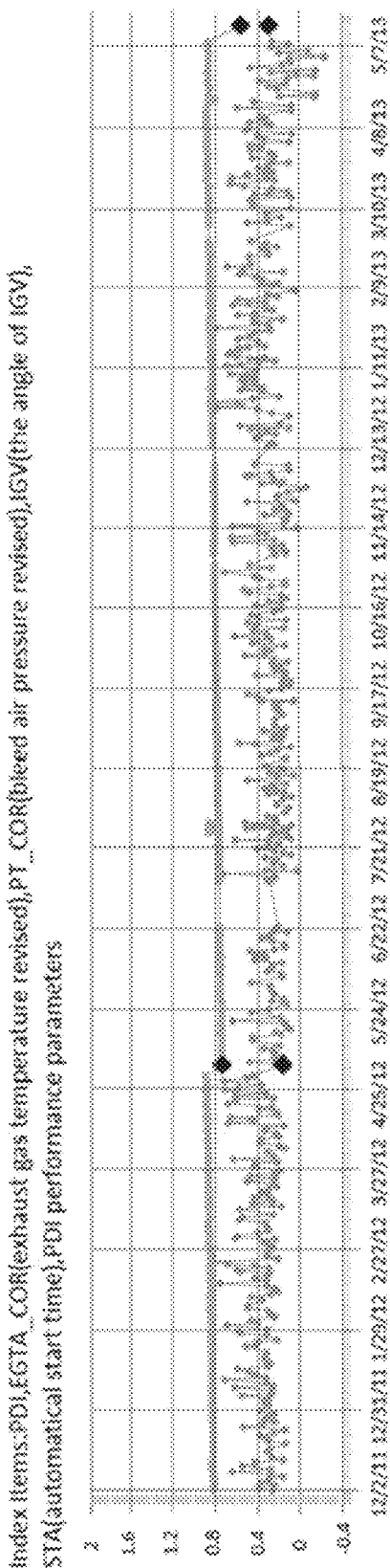
FIGS. 11A-11E are is a statistical data diagram of other operation parameters of APU in the example illustrated in FIG. 10.
Figure 11B:
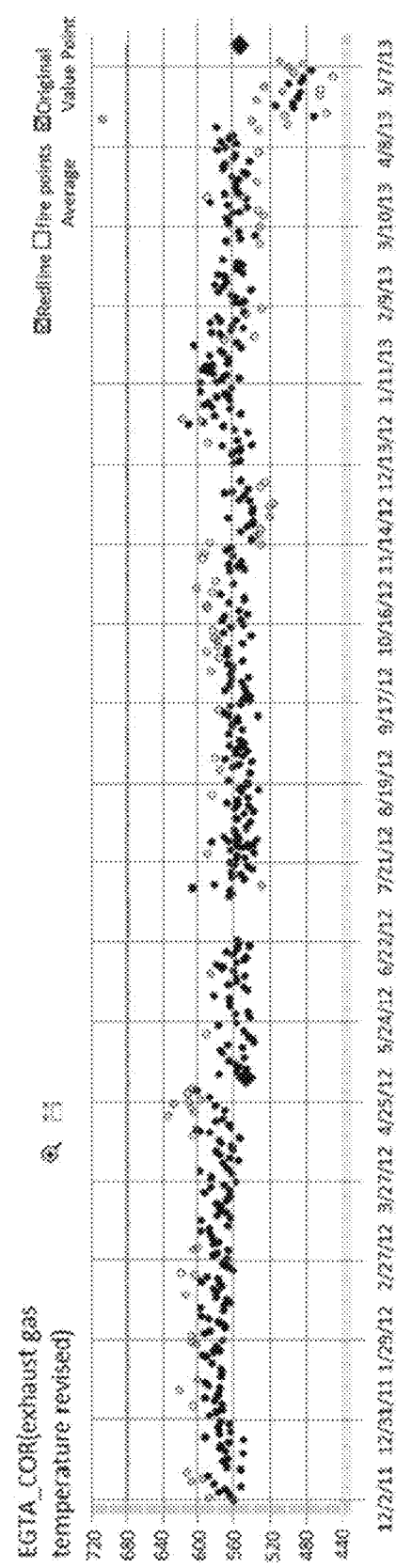
Figure 11C:
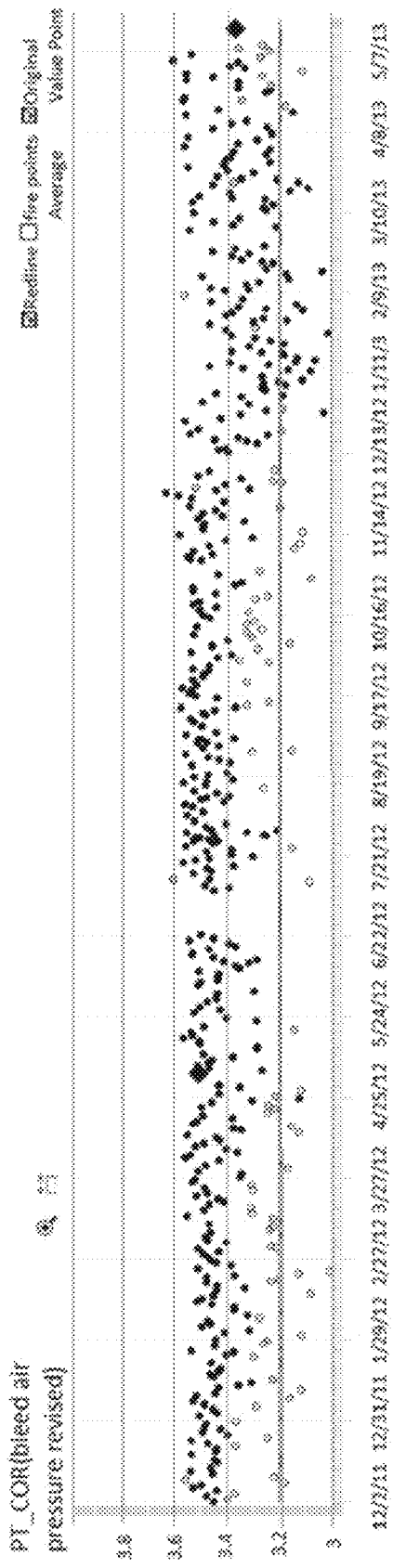
Figure 11D:
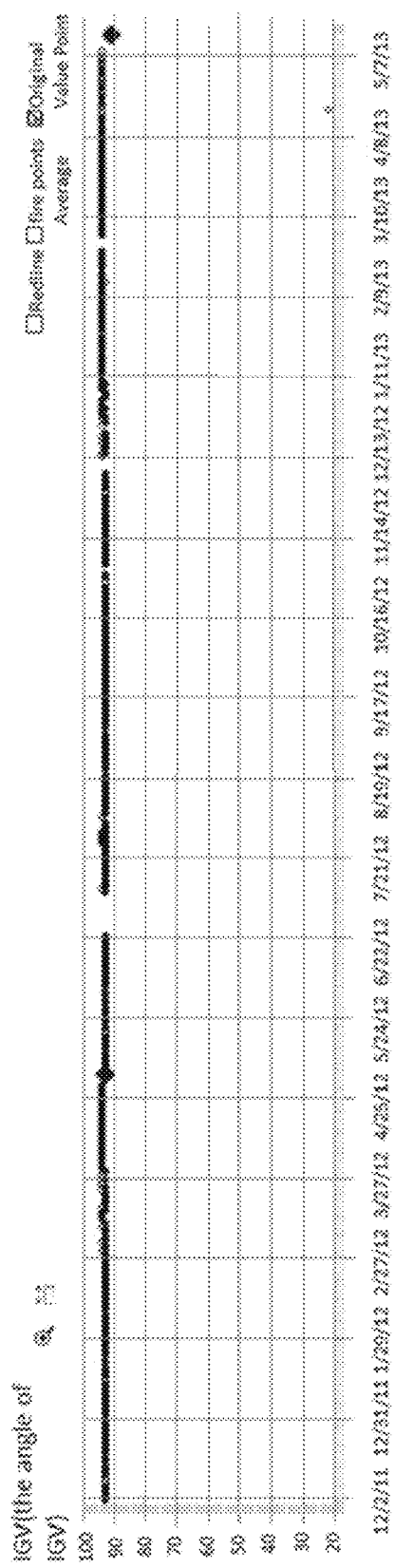
Figure 11E:
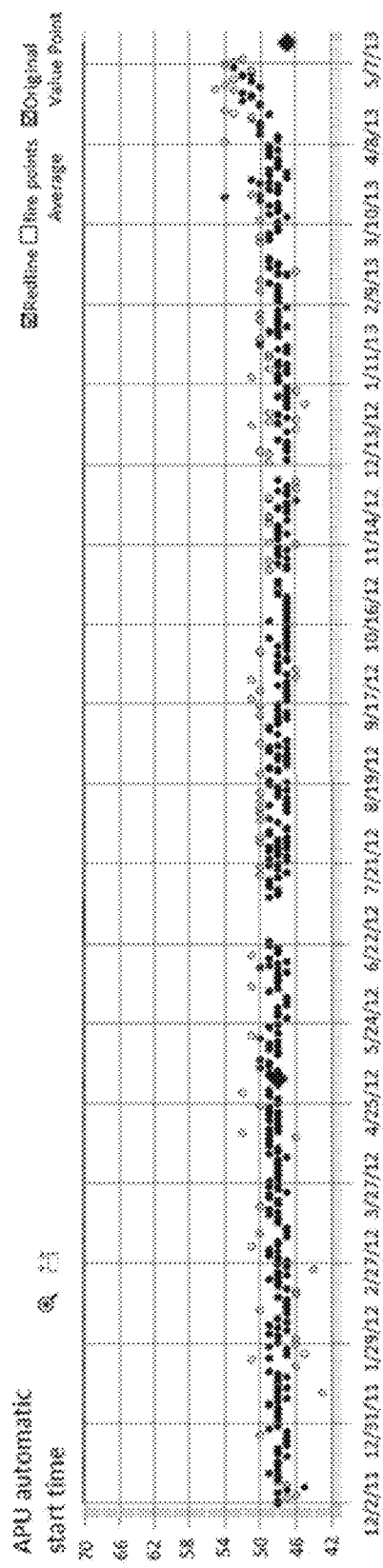
Figure 12A:
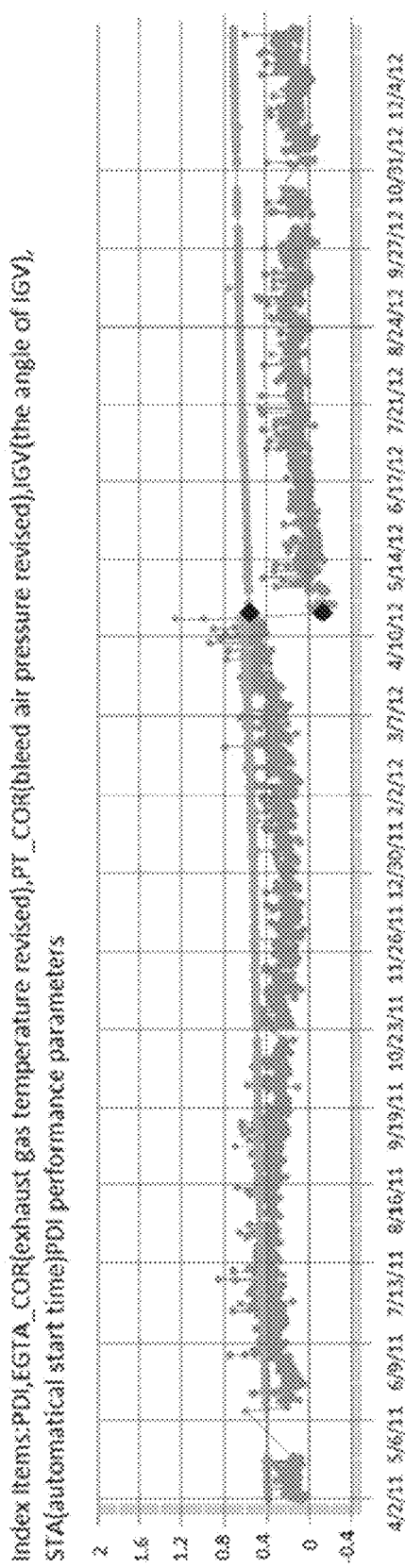
FIGS. 12A-12E are is a statistical data diagram recorded at the time of the malfunction of the turbine vane fracture and casing jam according to another example of the present invention.
Figure 12B:
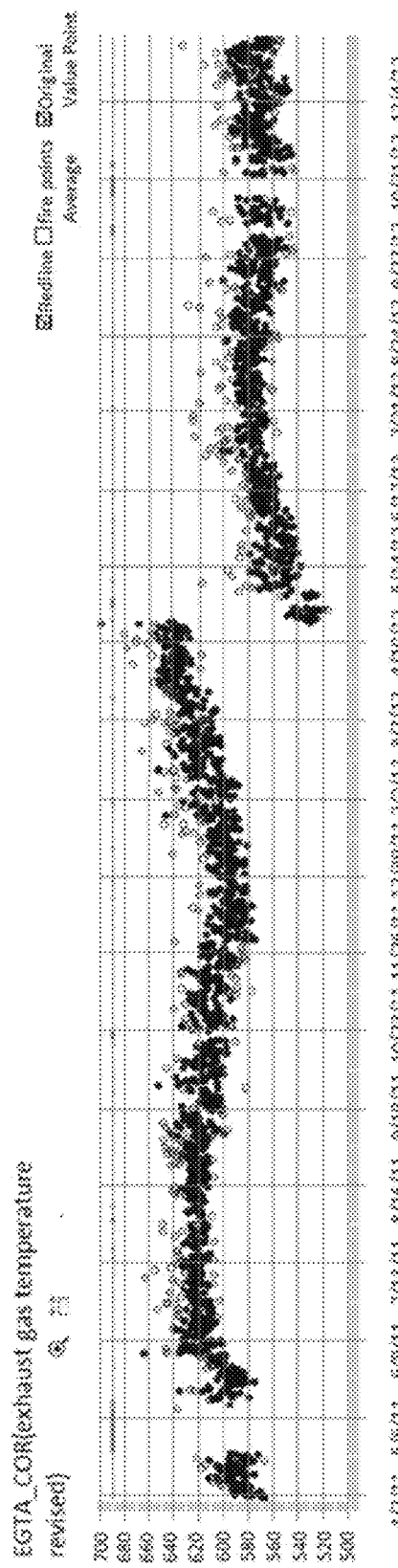
Figure 12C:
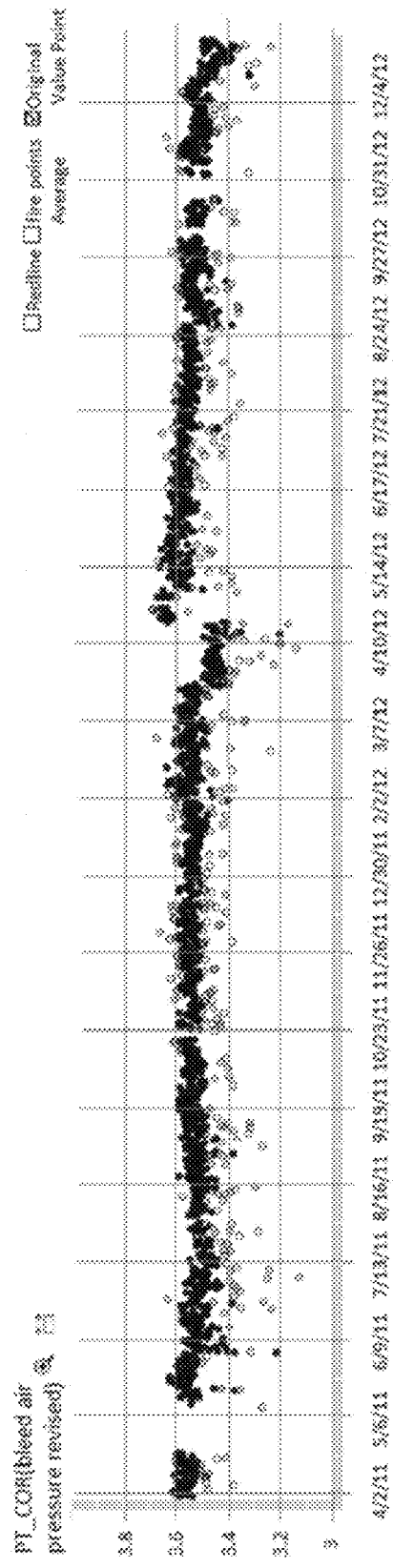
Figure 12D:
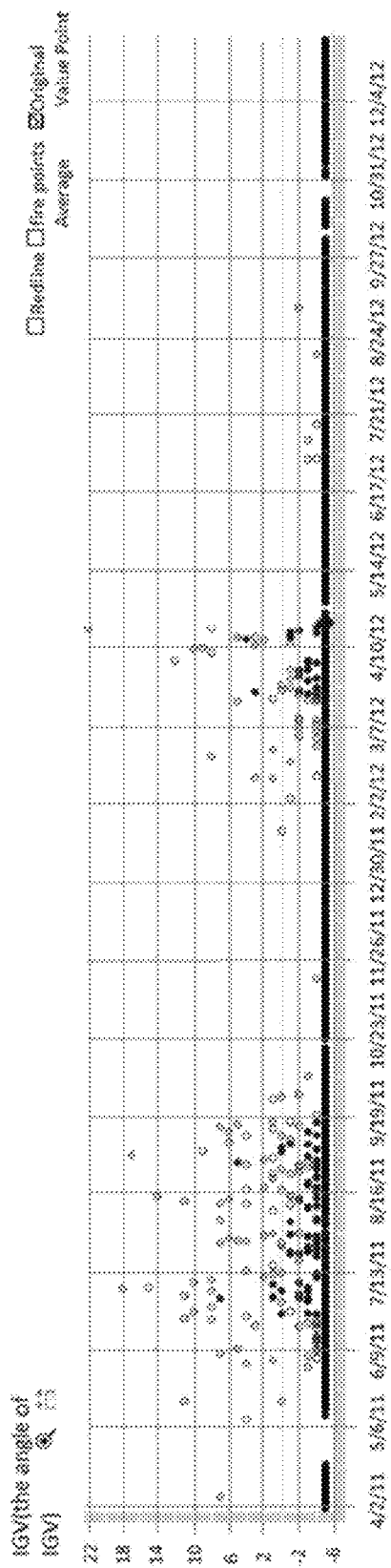
Figure 12E:
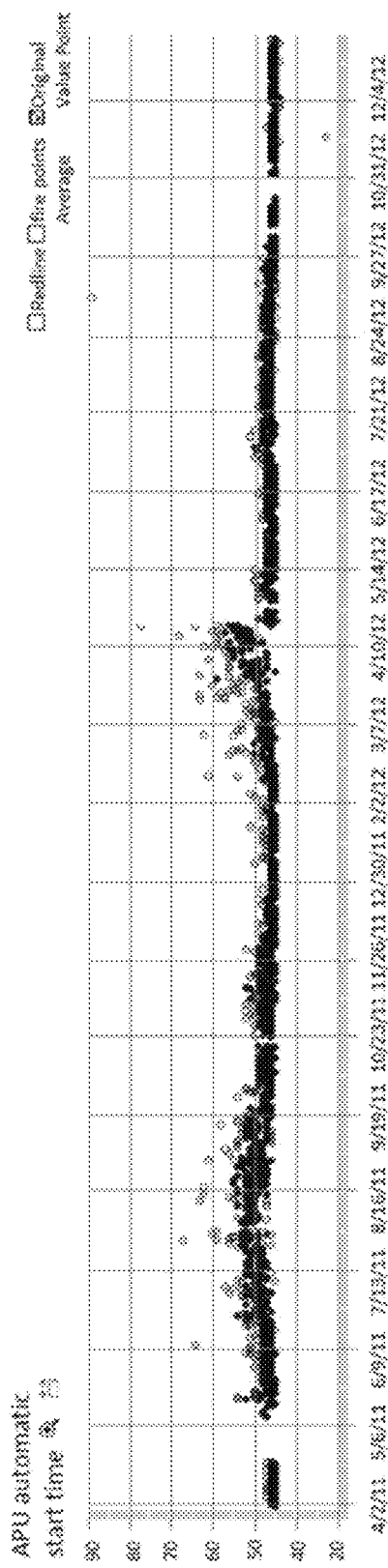

FIG. 7 is a flow diagram illustrating the method for monitoring the APU turbine and rotor shaft jam according to yet another example of the present invention. In the example of FIG. 7, the parameters the start time STA, exhausted gas temperature EGTA, the angle of inlet guide vane IGV and the temperature and rotation speed when EGT is at its peak are used.

As shown in FIG. 7, in method 7000 for monitoring the malfunction of the APU turbine vane fracture and rotor shaft jam, in step 7100, the following operation information of aircraft APU is acquired: the start time STA, exhausted gas temperature EGTA, the angle of inlet guide vane IGV and the temperature and rotation speed when EGT is at its peak. The methods in example in FIGS. 5 and 6 for acquiring the start time STA can also be used for acquiring the exhausted gas temperature EGTA, the angle of inlet guide vane IGV and the temperature and rotation speed when EGT is at its peak.

In step 7200, determining whether the start time STA is discrete. The method for determining whether the start time STA is discrete includes the examples of FIGS. 5 and 6. The other methods can also be applied in step 7200 to determine whether the start time STA is discrete.

In step 7300, judging whether the highest exhaust gas temperature on start EGTP is close to or reaches the redline value. This demonstrates that in the case of decreased efficiency, APU increase the gasoline injection amount to maintain the input power.

In step 7400, calculating NPA, and judging whether NPA is reduced to the predetermined threshold value. According to one example of the invention, the predetermined threshold value is about 35-40%.

In step 7500, if the exhausted gas temperature EGTP is close to or reaches the redline value and NPA is reduced to the predetermined threshold value, it can be judged that the malfunction of the APU turbine vane fracture and rotor shaft jam occurs.

According to one example of the invention, whether the malfunction of the APU turbine vane fracture and rotor shaft jam occurs can be further judged by EGT and IGV. In step 7600, judging whether the exhausted gas temperature EGT is close to or reaches the redline value or the angle of IGV increase or jump upward. This demonstrates that the exhausted gas temperature EGT reaches the redline value, and APU must increase the angle of IGV to reduce the input torque to ensure the constant rotation speed.

FIGS. 8A-8G are a statistical data diagram recorded at the time of the APU turbine and rotor shaft jam according to one example of the present invention. Wherein, the diamond marker represents replace of APU. It can be seen from FIGS. 8A-8G that the start time STA appears gradual raise as shown in solid line, and gradual restoration as shown in dotted line, and finally, closes to the final discrete state shown in diamond marker. FIGS. 8A-8G also show that the highest exhaust gas temperature on start EGTP is close to redline value 840 degree, and NPA is close to or even exceeds the predetermined threshold value 35%.

FIGS. 9A-9E are a statistical data diagram of other operation parameters of APU in the example illustrated in FIGS. 8A-8G. As shown in FIGS. 9A-9E, EGTA is close to redline value, while IGV appears a upward jump.

FIGS. 10A-10G are a statistical data diagram recorded at the time of the malfunction of the turbine vane fracture and casing jam according to one example of the present invention. Wherein, the diamond marker represents replace of APU. It can be seen from FIGS. 10A-10G that the start time STA also becomes discrete, the highest exhaust gas temperature on start EGTP is close to redline value 840, and NPA is close to or even exceeds the predetermined threshold value 40%.

FIGS. 11A-11E are a statistical data diagram of other operation parameters of APU in the example illustrated in FIGS. 10A-10G. As shown in FIGS. 11A-11E, EGTA decreases instead of being close to the redline value; and IGV is not adjusted. However, the actual condition is: the serious failure of the APU turbine vane fracture and rotor shaft jam occurs in this APU.

FIGS. 12A-12E are a statistical data diagram recorded at the time of the malfunction of the turbine vane fracture and casing jam according to another example of the present invention. FIGS. 12A-12E show more clearly the process that the start time STA raises gradually, returns to normal gradually, raises again gradually and returns to normal, and then disperse quickly, and finally is replaced. The example of FIGS. 12A-12E reflect the long-term regular of the change of STA, demonstrating the history data of STA is helpful for judging the malfunction of the APU turbine vane fracture and rotor shaft jam. This is beneficial to distinguishing the malfunction of the APU turbine vane fracture and rotor shaft jam with other malfunctions.

Figure 13:
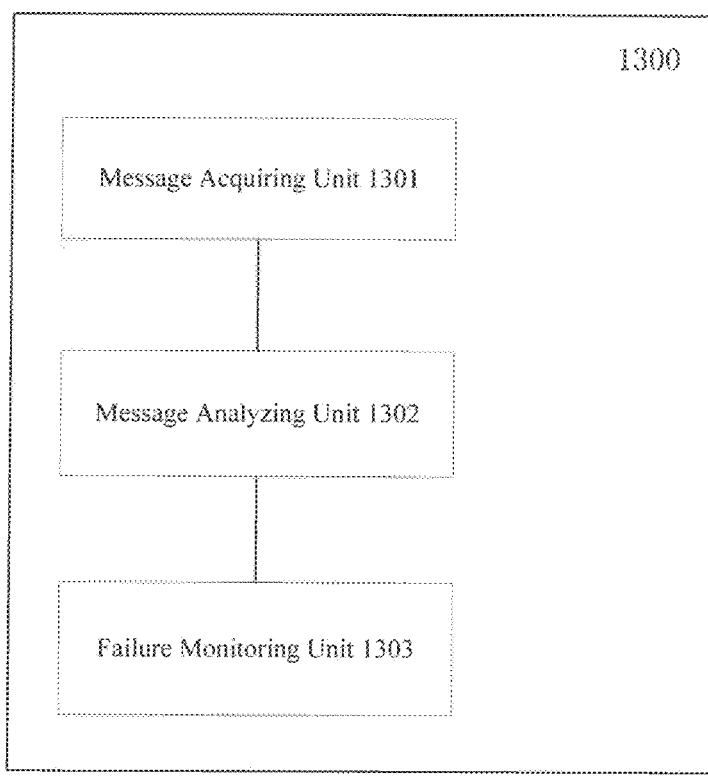
FIG. 13 is a device for monitoring the malfunction of the turbine vane fracture and rotor shaft jam of aircraft auxiliary power unit APU according to one example of the present invention.

FIG. 13 is a device for monitoring the malfunction of the turbine vane fracture and rotor shaft jam of aircraft auxiliary power unit APU according to one example of the present invention. As shown in FIG. 13, the device 1300 for monitoring the malfunction of the turbine vane fracture and rotor shaft jam of airborne auxiliary power unit APU comprises: message acquiring unit 1301, which acquires the APU message within a time period; message analyzing unit 1302, which analyzing the desired APU operation data, the operation data at least comprises the start time STA; and failure monitoring unit 1303, which determines the circumstance of the APU turbine vane fracture and rotor shaft jam is in stable phase, decline phase, serious decline phase or malfunction phase according to the operation data of APU.

According to one example of the invention, a device for monitoring the circumstances of turbine vane fracture and rotor shaft jam of aircraft auxiliary power unit APU is provided, which comprises: a processor; and a memory linked with the processor, which stores the computer-readable codes; the computer-readable codes run in the processor to execute the following steps: acquiring the APU messages at multiple time points within a time period; obtaining the operation parameters of the APU according to the APU message, the operation parameters at least comprises start time STA; calculating the average value AVG and deviation index $\delta$ of the start time STA within the time period; and determining that the circumstances of APU turbine vane fracture and rotor shaft jam is in stable phase, decline phase, serious decline phase or malfunction phase according to the deviation index $\delta$.

The method and device for monitoring the malfunction of the APU turbine vane fracture and rotor shaft jam according to the invention, can find the malfunction of the turbine vane fracture and casing jam of APU before the occurrence of serious circumstances such as the stop of APU, and the replacement is taken. In this way, a large cost for maintenance and stock will be reduced, and the maintenance cycle will be shortened.

The above examples are only described for illustrating the present invention, and do not mean to limit the present invention. A person with ordinary skill in relevant art may make various changes and variations without departing from the scope of the present invention. Therefore, all equivalent technical solutions shall also fall within the disclosure of the present invention.

We claim:

1. A method for monitoring a malfunction of an APU turbine vane fracture and rotation shaft jam, comprising:
   acquiring, by a message acquiring unit, APU messages at multiple time points within a period;
   obtaining, by a message analyzing unit, operation parameters of the APU according to the APU messages, the operation parameters of the APU including at least a start time STA;
   calculating, by a message analyzing unit, the average value AVG and the deviation index $\delta$ of the start time STA within the period;
   determining, by a malfunction monitoring unit, a circumstance of the APU turbine vane fracture and rotation shaft jam is in stable phase, decline phase or malfunction phase according to the deviation index $\delta$.

2. According to the method of claim 1, wherein the step of determining the circumstances of APU turbine vane fracture and rotor shaft jam is in stable phase, decline phase or malfunction phase comprises:
   in response to the deviation index $\delta$ is less than a threshold value of decline phase, determining, by the malfunction monitoring unit, the circumstances of APU turbine vane fracture and rotor shaft jam is in stable phase;
   in response to the deviation index $\delta$ is greater than the threshold value of decline phase and less than a threshold value of malfunction, determining, by the malfunction monitoring unit, the circumstances of APU turbine vane fracture and rotor shaft jam is in decline phase; and
   in response to the deviation index $\delta$ is greater than the threshold value malfunction, determining, by the malfunction monitoring unit, the circumstances of APU turbine vane fracture and rotor shaft jam is in malfunction phase.

3. According to the method of claim 2, further comprises:
   determining, by the malfunction monitoring unit, the deviation index $\delta$ when the circumstances of APU turbine vane fracture and rotor shaft jam is in stable phase;
   wherein the threshold value of decline is around 2 times than the deviation index $\delta$, and the threshold value of malfunction is around 6 times than a stable deviation index.

4. According to the method of claim 2, wherein, the decline phase further comprises a serious decline phase, and a threshold value of the serious decline phase is between the threshold value of decline phase and the threshold value of malfunction phase, in response to the deviation index $\delta$ is greater than the threshold value of the serious decline phase and less than the threshold value of the malfunction phase, determining, by the malfunction monitoring unit, the circumstances of APU turbine vane fracture and rotor shaft jam is in serious decline phase, the threshold value of the serious decline phase is around 4 times than the stable deviation index $\delta$.

5. According to the method of claim 1, wherein the time period is about 5-10 days in the case when 2 or 3 time points are measured per day.

6. According to the method of claim 1, wherein about 10-40 APU messages are obtained within the time period.

7. According to the method of claim 1, further comprises:
   Obtaining, by a message analyzing unit, the start time STA on a next time point by updating the APU message at the next time point;
   in response to $STA_{next}$ is greater than $AVG+n\delta$ or less than $AVG-n\delta$, determining, by the malfunction monitoring unit, whether $STA_{next+1}$ obtained according to the further next message related to APU is greater than $AVG+n\delta$ or less than $AVG-n\delta$; and in response to the start time STA obtained according to the message related to APU is greater than AVG+nδ or less than AVG−nδ continuously and exceeding a predetermined number Z, issuing, by the malfunction monitoring unit, a warning, wherein the value of n is determined by a control strategy.

8. According to the method of claim 7, in response to the start time STA obtained according to the message related to APU is between AVG+nδ or less than average value AVG−nδ, recalculating, by the message analyzing unit, the average value AVG and deviation index δ of the start time STA.

9. According to the method of claim 7, in response to the start time STA obtained according to the message related to APU is greater than AVG+nδ or less than AVG−nδ continuously and exceeding the predetermined number Z, recalculating, by the message analyzing unit, the average value AVG and deviation index δ of the start time STA.

10. According to the method of claim 1, wherein the deviation index δ is the standard deviation of the start time STA.

11. According to the method of claim 7, wherein the value of n is 2 or 3.

12. According to the method of claim 7, further comprises:

in response to the start time STA obtained according to the message related to APU is greater than AVG+nδ or less than AVG−nδ continuously and exceeding the predetermined number Z, issuing, by the malfunction monitoring unit, the warning.

13. According to the method of claim 7, wherein the value of Z is 3-5.

14. According to the method of claim 1, the method further comprises: in response to whether a highest exhaust gas temperature on start EGTP reaches a redline temperature, issuing, by the malfunction monitoring unit, a warning of the malfunction of the turbine vane fracture and rotation shaft jam.

15. According to the method of claim 14, the method further comprises: in response to whether a number of proportion in APU (NPA) reaches or closes to a predetermined threshold value of NPA when EGT is at its peak on start, issuing, by the malfunction monitoring unit, the warning of the malfunction of the turbine vane fracture and rotor shaft jam, wherein the predetermined threshold value of NPA is 35-40%, wherein the NPA is the percent of the rotation speed of the turbine when the exhaust temperature (EGT) of APU reaches its peak value in the start stage of APU with respect to the constant rotation speed in normal operation of APU (% RPM/APU RPM).

16. According to the method of claim 15, wherein in response to an increase of the standard of EGTP and NPA, issuing, by the malfunction monitoring unit, the warning of the malfunction of the turbine vane fracture and rotation shaft jam.

17. According to the method of claim 15, the method further comprises: in response to an exhaust gas temperature EGT close to the redline temperature or whether an angle of an inlet guide vane IGV appears as an upward jump, issuing, by the malfunction monitoring unit, the warning of the malfunction of APU turbine vane fracture and rotation shaft jam.

18. According to the method of claim 1, wherein the method further comprises:

obtaining, by the message analyzing unit, history data of the start time STA; and determining, by the malfunction monitoring unit, whether the start time STA exhibits gradual increase, gradual regular, and then discrete.

19. A device for monitoring a malfunction of an airborne auxiliary power unit APU turbine vane fracture and rotation shaft jam, comprises:

a message acquiring unit, which acquires APU messages within a time period;

a message analyzing unit, which analyses required APU operation data at least comprising a start time STA and calculates average value AVG and deviation index δ of the start time STA within the time period; and a malfunction monitoring unit, which determines circumstances of APU turbine vane fracture and rotor shaft jam is in stable phase, decline phase or malfunction phase according to the deviation index δ.

20. A device for monitoring a malfunction of an airborne auxiliary power unit APU turbine vane fracture and rotation shaft jam, comprises:

a processor; and a memory coupled to the processor, which stores computer-readable codes;

the computer-readable codes run in the processor to execute the following steps:

acquiring APU messages at multiple time points within a time period;

obtaining operation parameters of the APU according to the APU message, the operation parameters at least comprises start time STA;

calculating average value AVG and deviation index δ of the start time STA within the time period; and determining that circumstances of APU turbine vane fracture and rotor shaft jam is in stable phase, decline phase, serious decline phase or malfunction phase according to the deviation index δ.

* * * * *